US012774341B2

(12) United States Patent
Chen et al.

(10) Patent No.: US 12,774,341 B2
(45) Date of Patent: Oct. 27, 2026

(54) ANTIBODIES BINDING BCMA AND USES THEREOF

(71) Applicant: Biosion Inc., Nanjing (CN)

(72) Inventors: Mingjiu Chen, Nanjing (CN); Wei Tan, Nanjing (CN); Cathy Xiaoyan Zhong, Nanjing (CN); Shukai Xia, Nanjing (CN)

(73) Assignee: BIOSION INC., Nanjing (CN)

( * ) Notice: Subject to any disclaimer, the term of this patent is extended or adjusted under 35 U.S.C. 154(b) by 1159 days.

(21) Appl. No.: 17/788,926

(22) PCT Filed: Dec. 29, 2020

(86) PCT No.: PCT/CN2020/141099
§ 371 (c)(1),
(2) Date: Jun. 24, 2022

(87) PCT Pub. No.: WO2021/136308
PCT Pub. Date: Jul. 8, 2021

(65) Prior Publication Data
US 2023/0055711 A1 Feb. 23, 2023

Related U.S. Application Data

(60) Provisional application No. 62/956,642, filed on Jan. 3, 2020.

(51) Int. Cl.
*C07K 16/28* (2006.01)
*A61K 47/68* (2017.01)

(52) U.S. Cl.
CPC ...... *C07K 16/2878* (2013.01); *A61K 47/6817* (2017.08); *A61K 47/6849* (2017.08);
(Continued)

(58) Field of Classification Search
None
See application file for complete search history.

(56) References Cited

U.S. PATENT DOCUMENTS 10,072,088 B2 * 9/2018 Pillarisetti ............... A61P 35/00
10,465,009 B2 * 11/2019 Armitage ........... C07K 16/2878
(Continued)

FOREIGN PATENT DOCUMENTS

CN 109485733 A 3/2019
JP 2019512464 A 5/2019
(Continued)

OTHER PUBLICATIONS

Tai et al., Novel anti-B-cell maturation antigen antibody-drug conjugate (GSK2857916) selectively induces killing of multiple myeloma, Blood, 123(20):3128-3138, May 15, 2014.*
(Continued)

*Primary Examiner* — Claire Kaufman
(74) *Attorney, Agent, or Firm* — Duane Morris LLP; Thomas J. Kowalski

(57) ABSTRACT

An isolated monoclonal antibody that specifically binds human BCMA, or the antigen-binding portion thereof. The present disclosure further provides an immunoconjugate, a bispecific molecule, a chimeric antigen receptor, or an oncolytic virus comprising the antibody or the antigen-binding portion thereof, as well as a nucleic acid molecule encoding the same.

17 Claims, 5 Drawing Sheets

Specification includes a Sequence Listing.

| | Mouse B1H2 | Chimeric B1H2 | huB1H2-V33 | huB1H2-V10 | BCMA BM1 |
|---|---|---|---|---|---|
| IC50 | 0.2819 | 0.2648 | 1.447 | 1.515 | 2.894 |

(52) U.S. Cl.
CPC .... *C07K 2317/24* (2013.01); *C07K 2317/732* (2013.01); *C07K 2317/76* (2013.01)

(56) References Cited

U.S. PATENT DOCUMENTS

| | | | | |
|---|---|---|---|---|
| 10,683,369 | B2 * | 6/2020 | Vu | C07K 16/468 |
| 11,447,559 | B2 * | 9/2022 | Choi | C07K 16/28 |

FOREIGN PATENT DOCUMENTS

| | | | |
|---|---|---|---|
| KR | 20180107111 | A | 10/2018 |
| WO | 2016090327 | A2 | 6/2016 |
| WO | 2017143069 | A1 | 8/2017 |
| WO | 2019/053611 | A1 | 3/2019 |
| WO | 2019066435 | A2 | 4/2019 |
| WO | 2019190969 | A1 | 10/2019 |

OTHER PUBLICATIONS

Googlish et al., The Role of Fc Receptors on the Effectiveness of Therapeutic Monoclonal Antibodies. Int. J. Mol. Sci. 22, 8947, 25 pages, 2021.*

Trudel Suzanne et al., Deep and durable responses in patients (pts) with relapsed/refractory multiple myeloma (MM) treated with monotherapy GSK2857916, an antibody drug conjugate against B-cell maturation antigen (BCMA): preliminary results from part 2 of study BMA117159, Blood, vol. 130, Supplement 1, Dec. 8, 2017, p. 741.

Oden Felix, et al. Potent anti-tumor response by targeting B cell maturation antigen (BCMA) in a mouse model of multiple myeloma. Mol Oncol. Aug. 2015;9(7):1348-58.

European Search Report and Opinion issued by EPO on Dec. 11, 2023, in counterpart EP Application No. 20910567.

Office Action issued by KIPO on Nov. 14, 2024, in counterpart Korean Application No. 10-2022-7020541.

Office Action issued by JPO on Aug. 8, 2023, in counterpart Japanese Application No. 2022-535936.

Cho, et al., Targeting B Cell Maturation Antigen (BCMA) in Multiple Myeloma: Potential Uses of BCMA-Based Immunotherapy, Frontiers in Immunology (Aug. 2018) vol. 9, Article 1821, p. 1-15.

International Search Report issued Mar. 25, 2021, in International Application No. PCT/CN2020/141099.

* cited by examiner

| | Mouse B1H2 | BCMA BM1 |
|---|---|---|
| EC50 | 0.7018 | 1.113 |

| | Mouse B1H2 | BCMA BM1 |
|---|---|---|
| EC50 | 0.8855 | 17.68 |

| | Mouse B1H2 | BCMA BM1 |
|---|---|---|
| IC50 | 6.095 | 10.67 |

| | Mouse B1H2 | BCMA BM1 |
|---|---|---|
| IC50 | 1.026 | 2.642 |

| | Mouse B1H2 | Chimeric B1H2 | huB1H2-V33 | huB1H2-V10 | BCMA -BM1 |
|---|---|---|---|---|---|
| EC50 | 0.1774 | 0.2262 | 0.4386 | 0.4696 | 0.5685 |

| | Mouse B1H2 | Chimeric B1H2 | huB1H2-V33 | huB1H2-V10 | BCMA BM1 |
|---|---|---|---|---|---|
| EC50 | 31.35 | 189.5 | ~176.5 | ~25385 | 0.186 |

| | Mouse B1H2 | Chimeric B1H2 | huB1H2-V33 | huB1H2-V10 | BCMA BM1 |
|---|---|---|---|---|---|
| EC50 | 0.6134 | 0.9531 | 0.8651 | 1.201 | 8.86 |

| | Mouse B1H2 | Chimeric B1H2 | huB1H2-V33 | huB1H2-V10 | BCMA BM1 |
|---|---|---|---|---|---|
| IC50 | 8.278 | 9.715 | 7.055 | 10.2 | 12.56 |

| | Mouse B1H2 | Chimeric B1H2 | huB1H2-V33 | huB1H2-V10 | BCMA BM1 |
|---|---|---|---|---|---|
| IC50 | 0.2819 | 0.2648 | 1.447 | 1.515 | 2.894 |

| | BCMA BM1 | huB1H2-V10 | Chimeric B1H2 |
|---|---|---|---|
| EC50 | 0.2867 | 0.09156 | 0.04176 |

| | BCMA BM1 | huB1H2-V33 | Chimeric B1H2 |
|---|---|---|---|
| EC50 | 0.2353 | 0.1186 | 0.04377 |

| | BCMA BM 1+DT3C | huB1H2-V10+DT3C | huB1H2-V33+DT3C |
|---|---|---|---|
| IC50 | 1.549 | 0.1867 | 0.14 |

ANTIBODIES BINDING BCMA AND USES THEREOF

RELATED APPLICATIONS AND INCORPORATION BY REFERENCE

This application claims priority to U.S. provisional application No. 62/956,642 filed on Jan. 3, 2020.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The Sequence Listing for this application is labeled "55532-00050 SequenceListing" which was created on Dec. 28, 2020, revised on May 22, 2026 and is 41,270 bytes in size. The entire content of the sequence listing is incorporated herein by reference in its entirety.

FIELD OF THE INVENTION

The present disclosure relates generally to an isolated monoclonal antibody, particularly a mouse, chimeric or humanized monoclonal antibody, or an antigen-binding portion thereof, that specifically binds to human BCMA with high affinity and functionality. A nucleic acid molecule encoding the antibody or antigen-binding portion, an expression vector, a host cell and a method for expressing the antibody or antigen-binding portion are also provided. The present disclosure further provides an immunoconjugate, a bispecific molecule, a chimeric antigen receptor, and an oncolytic virus containing the antibody or antigen-binding portion thereof, as well as a diagnostic or treatment method using the antibody or antigen-binding portion thereof of the disclosure.

BACKGROUND OF THE INVENTION

B cell maturation antigen (BCMA), also termed tumor necrosis factor receptor superfamily member 17 (TNFRS17), is a transmembrane protein having a cysteine-rich extracellular domain (Madry C et al., (1998) *Int Immunol.* 10(11):1693-702; Laabi Y et al., (1994) *Nucleic Acids Res* 22(7):1147-54; Laabi Y et al., (1992) *EMBO J* 11(11):3897-904). It, along with two TNFR superfamily members BAFF-R and TACI, regulates humoral immunity, B-cell development and homeostasis, especially B cell proliferation, survival, maturation and differentiation into plasma cells (PC) (Mackay F et al., (2003) *Annu Rev Immunol* 21:231-64; Marsters S A et al., (2000) *Curr Biol* 10(13):785-8; Gross J A et al., (2000), *Nature* 404(6781):995-9; Thompson J S et al., (2000) *J Exp Med* 192(1):129-35). BCMA is also important for long-lived PC survival.

BCMA is exclusively expressed on the surfaces of plasmablasts and differentiated PCs, more highly on malignant than normal PCs (Carpenter R O et al., (2013) *Clin Cancer Res* 19(8):2048-60; O'Connor B P et al., (2004) *J Exp Med* 199(1):91-8; Benson M J et al., (2008) *J Immunol* 180(6):3655-9; Yang M et al., (2005) *J Immunol* 175(5):2814-24; Avery D T et al., (2003) *J Clin Invest* 112(2):286-97; Novak A J et al., (2004) *Blood* 103(2):689-94; Chiu A et al., (2007) *Blood* 109(2):729-39; Lee L et al., (2018) *Blood* 131(7):746-58; Carpenter R O et al., (2013) supra; Tai Y T et al., (2014) *Blood* 123(20):3128-38; Claudio J O et al., (2002) *Blood* 100(6):2175-86; Seckinger A et al., (2017) *Cancer Cell* 31(3):396-410), and reported to be involved in leukemia, lymphomas and multiple myeloma. For example, elevated plasma BCMA levels were observed in patients with chronic lymphocytic leukemia and correlated with clinical statuses (Kyle A Udd et al., (2015) *Blood.* 126(23):2931). BCMA was also found to be highly expressed in multiple myeloma tumor cells, and BCMA overexpression or APRIL binding to BCMA in these cells significantly promotes cell growth and survival in vivo (Tai Y T et al., (2016) *Blood* 127(25):3225-36; Matthes T et al., (2011) *Blood* 118(7):1838-44). Further, APRIL and BAFF, via binding to BCMA and TACI, further activate NFκB pathways and upregulate anti-apoptotic proteins (Mcl-1, Bcl-2, Bcl-xL) to protect multiple myeloma tumor cells against dexamethasone- and serum deprivation-induced cell death (Moreaux J et al., (2004) *Blood* 103(8):3148-57; Neri P et al., (2007) *Clin Cancer Res* 13(19):5903-9; Shen X et al., (2016) *Cell Biochem Funct* 34(2):104-10).

As the second prevalent hematopoietic malignancy, multiple myeloma is a clonal B-cell malignancy that occurs in multiple sites within the bone marrow before spreading to the circulation, either de novo, or as a progression from monoclonal gammopathy of undetermined significance (MGUS). It is commonly characterized by increases in paraprotein and osteoclast activity, as well as hypercalcaemia, cytopenia, renal dysfunction, hyperviscosity and peripheral neuropathy. Decreases in both normal antibody levels and numbers of neutrophils are also common, leading to a life-threatening susceptibility to infection. Two monoclonal antibodies targeting CD38 and SLAMF7 were approved in late 2015 for the treatment of relapsed and refractory multiple myeloma, but the wide expression of two antigens in normal tissues limited their long-term clinical use. In contrast, BCMA has emerged as a potential therapeutic target because of its restricted expression pattern and unique transmembrane structure. The first therapeutic anti-BCMA antibody-drug conjugate (ADC), GSK2857916, rapidly eliminates multiple myeloma cells in two murine models and significantly prolongs mice survival (Tai Y T et al., (2014) supra). Another anti-BCMA ADC, HDP-101, has shown in vitro cytotoxicity against multiple myeloma cells at picomolar range, resulting in significant tumor regression with good tolerance. Several anti-BCMA CAR-T cell therapies have also shown impressive clinical outcomes (Shih-Feng Cho et al., (2018) *Frontiers in Immunology* 9:1821).

Ongoing efforts are attempting to find more BCMA binding moieties, including antibodies, that are more potent and safe.

Citation or identification of any document in this application is not an admission that such document is available as prior art to the present disclosure.

SUMMARY OF THE INVENTION

The present disclosure provides an isolated monoclonal antibody, for example, a mouse, human, chimeric or humanized monoclonal antibody, or an antigen-binding portion thereof, that binds to BCMA (e.g., the human BCMA) and has comparable, if not higher, binding affinity to BCMA and blocking activity on BCMA-BAFF binding as compared to prior art anti-BCMA antibodies such as the BCMA-binding portion of GSK2857916. The anti-BCMA antibodies of the disclosure also induce higher antibody dependent cell mediated cytotoxicity (ADCC) at certain concentrations, e.g., at low concentrations, as compared to prior art anti-BCMA antibodies such as the BCMA-binding portion of GSK2857916.

The antibody or antigen-binding portion of the disclosure can be used for a variety of applications, including detection of the BCMA protein, and treatment and prevention of BCMA associated diseases, such as cancers and infectious diseases.

Accordingly, in one aspect, the disclosure pertains to an isolated monoclonal antibody (e.g., a mouse, chimeric or humanized antibody), or an antigen-binding portion thereof, that binds BCMA, having i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to SEQ ID NOs: 1, 2 and 3, respectively; and/or a light chain variable region that may comprise a VL CDR1 region, a VL CDR2 region and a VL CDR3 region, wherein the VL CDR1 region, the VL CDR2 region, and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to SEQ ID NOs: 4, 5 and 6, respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 7, 8, or 9 (X1=V, X2=R, X3=T; X1=M, X2=R, X3=T; X1=V, X2=S, X3=T; X1=V, X2=R, X3=K; or X1=V, X2=S, X3=K). The amino acid sequence set forth in SEQ ID NO: 7 may be encoded by nucleotide sequences of SEQ ID NOs: 17 or 24. The amino acid sequence set forth in SEQ ID NO: 9 (X1=V, X2=S, X3=T) may be encoded by the nucleotide sequence of SEQ ID NO: 18.

The light chain variable region may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 10 or 11 (X1=T, X2=V, X3=Y, X4=F; X1=A, X2=P, X3=F, X4=L; X1=A, X2=P, X3=Y, X4=L; X1=A, X2=V, X3=F, X4=L; or X1=A, X2=P, X3=F, X4=F). The amino acid sequence set forth in SEQ ID NO: 10 may be encoded by nucleotide sequences of SEQ ID NO: 19 or 25. The amino acid sequence set forth in SEQ ID NO: 11 (X1=A, X2=P, X3=F, X4=F) may be encoded by the nucleotide sequence of SEQ ID NO: 20.

The isolated monoclonal antibody or antigen-binding portion thereof of the present disclosure may comprise a heavy chain variable region and a light chain variable region, the heavy chain variable region and the light chain variable region may comprise amino acid sequences set forth in (1) SEQ ID NOs: 7 and 10, respectively; (2) SEQ ID NOs: 8 and 11 (X1=T, X2=V, X3=Y, X4-F; X1=A, X2=P, X3=F, X4-L; X1=A, X2=P, X3=Y, X4=L; or X1=A, X2=V, X3-F, X4=L), respectively; (3) SEQ ID NOs: 9 (X1=V, X2=R, X3=T; X1=M, X2=R, X3=T; X1=V, X2-S, X3=T; X1=V, X2=R, X3=K; or X1=V, X2-S, X3=K) and 11 (X1=T, X2=V, X3=Y, X4=F), respectively; (4) SEQ ID NOs: 9 (X1=V, X2=R, X3-T; X1=M, X2=R, X3-T; X1=V, X2-S, X3=T; X1=V, X2=R, X3=K; or X1=V, X2-S, X3=K) and 11 (X1=A, X2=P, X3=F, X4-L), respectively; (5) SEQ ID NOs: 9 (X1=V, X2=R, X3=T; X1=M, X2=R, X3=T; X1=V, X2-S, X3=T; X1=V, X2-R, X3-K; or X1=V, X2-S, X3=K) and 11 (X1=A, X2=P, X3=Y, X4-L), respectively; (6) SEQ ID NOs: 9 (X1=V, X2=R, X3=T; X1=M, X2=R, X3=T; X1=V, X2=S, X3=T; X1=V, X2-R, X3-K; or X1=V, X2-S, X3=K) and 11 (X1=A, X2=V, X3-F, X4-L), respectively; (7) SEQ ID NOs: 9 (X1=V, X2=S, X3-T) and 11 (X1=A, X2=P, X3=F, X4=F), respectively.

The isolated monoclonal antibody or antigen-binding portion thereof of the present disclosure may comprise a heavy chain and a light chain, the heavy chain comprising a heavy chain variable region and a heavy chain constant region, the light chain comprising a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region comprise amino acid sequences described above. The heavy chain constant region may be human IgG1 constant region having an amino acid sequence set forth in e.g., SEQ ID No: 12, or a functional fragment thereof, and the light chain constant region may be human kappa constant region having an amino acid sequences set forth in e.g., SEQ ID No: 13, or a functional fragment thereof. The amino acid sequences set forth in SEQ ID NOs: 12 and 13 may be encoded by nucleotide sequences of SEQ ID NO: 21 and 22, respectively.

The antibody of the present disclosure in some embodiments may comprise or consist of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above. The antibody of the disclosure can be a full-length antibody, for example, of an IgG1, IgG2 or IgG4 isotype. The antibody of the present disclosure in other embodiments may be a single chain variable fragment (scFv) antibody, or antibody fragments, such as Fab or Fab'2 fragments.

The antibody or antigen-binding portion thereof of the present disclosure has comparable, if not higher, binding affinity/capacity to human BCMA and BCMA-BAFF blocking activity than prior art anti-BCMA antibodies such as the BCMA binding portion of GSK2857916. The antibody or antigen-binding portion thereof of the disclosure also induces higher antibody dependent cell mediated cytotoxicity (ADCC) at certain concentrations, e.g., at low concentrations, as compared to prior art anti-BCMA antibodies such as the BCMA-binding portion of GSK2857916.

The disclosure also provides an immunoconjugate, such as an antibody-drug conjugate, comprising the antibody or antigen-binding portion thereof of the disclosure, linked to a therapeutic agent, such as a cytotoxin, e.g., a recombinant protein DT3C comprising diphtheria toxin (DT) lacking the receptor-binding domain and the C1, C2, and C3 domains of *Streptococcus* protein G (3C). When conjugated with a cytotoxin such as DT3C, the antibody or antigen-binding portion thereof of the disclosure is more quickly internalized by cells and shows higher target cell killing activity than prior art anti-BCMA antibodies such as the BCMA-binding portion of GSK2857916. The disclosure also provides a bispecific molecule comprising the antibody or antigen-binding portion thereof of the disclosure, linked to a second functional moiety (e.g., a second antibody) having a different binding specificity than said antibody or antigen-binding portion thereof. In another aspect, the antibody or antigen binding portion thereof of the present disclosure can be part of a chimeric antigen receptor (CAR). Also provided is an immune cell comprising the antigen chimeric receptor, such as a T cell. The antibody or antigen binding portion thereof of the present disclosure can also be encoded by or used in conjunction with an oncolytic virus.

A nucleic acid molecule encoding the antibody or antigen-binding portion thereof, the immunoconjugate, the bispecific molecule, or the CAR, of the disclosure is also encompassed by the disclosure, as well as an expression vector comprising such a nucleic acid molecule and a host cell comprising such an expression vector. A method for preparing the antibody or antigen-binding portion thereof, the immunoconjugate, the bispecific molecule, or the CAR of the disclosure using the host cell is also provided, comprising steps of (i) expressing the antibody or antigen-binding portion thereof, the immunoconjugate, the bispecific molecule, or the CAR in the host cell and (ii) isolating the antibody or antigen-binding portion thereof, the immunoconjugate, the bispecific molecule, or the CAR from the host cell or its cell culture.

A pharmaceutical composition comprising the antibody or antigen-binding portion thereof, the immunoconjugate, the bispecific molecule, the CAR, the immune cell, the oncolytic virus, the nucleic acid molecule, the expression vector or the host cell of the disclosure, and a pharmaceutically acceptable carrier, is also provided.

In yet another aspect, the disclosure provides a method for treating a tumor associated with increased BCMA expression, comprising administering to a subject a therapeutically effective amount of the pharmaceutical composition of the present disclosure. The tumor may be leukemia, lymphomas or multiple myeloma. In some embodiments, at least one additional anti-cancer antibody can be administered with the pharmaceutical composition of the disclosure, such as an anti-VISTA antibody, an anti-PD-1 antibody, an anti-PD-L1 antibody, an anti-LAG-3 antibody, an anti-CTLA-4 antibody, an anti-TIM-3 antibody, an anti-STAT3 antibody, and/or an anti-ROR1 antibody. In yet another embodiment, the subject is further administered with a cytokine (e.g., IL-2, IL-21, GM-CSF and/or IL-4), or a costimulatory antibody (e.g., an anti-CD137 and/or anti-GITR antibody). The antibody or antigen-binding portion thereof of the present disclosure may be, for example, mouse, human, chimeric or humanized.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
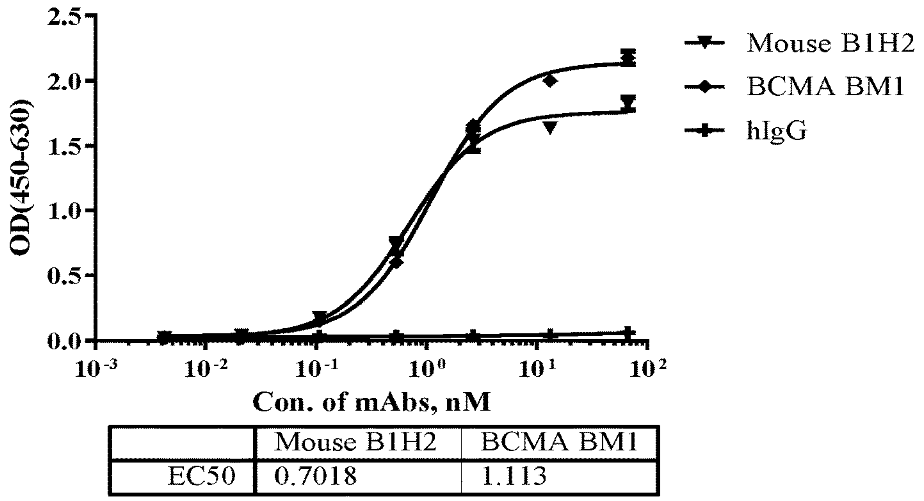
FIG. 1 shows the binding capacity of mouse antibody B1H2 to human BCMA in a capture ELISA.

To ensure that the present disclosure may be more readily understood, certain terms are first defined. Additional definitions are set forth throughout the detailed description.

The term "BCMA" refers to B cell maturation antigen, or tumor necrosis factor receptor superfamily member 17. The term "BCMA" comprises variants, isoforms, homologs, orthologs and paralogs. For example, an antibody specific for a human BCMA protein may, in certain cases, cross-react with a BCMA protein from a species other than human, such as monkey. In other embodiments, an antibody specific for a human BCMA protein may be completely specific for the human BCMA protein and exhibit no cross-reactivity to other species or of other types, or may cross-react with BCMA from certain other species but not all other species.

The term "human BCMA" refers to a BCMA protein having an amino acid sequence from a human, such as the amino acid sequence of human BCMA having a Genbank accession number of NP_001183.2. The terms "monkey or rhesus BCMA" and "mouse BCMA" refer to monkey and mouse BCMA sequences, respectively, e.g. those with the amino acid sequences having Genbank Accession Nos. XP_001106892.1 and NP_035738.1, respectively.

The term "antibody" as referred to herein includes whole antibodies and any antigen binding fragment (i.e., "antigen-binding portion") or single chains thereof. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" or "antigen-binding fragment" of an antibody (or simply "antibody portion"), as used herein, refers to one or more fragments of an antibody that retain the ability to specifically bind to an antigen (e.g., a BCMA protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a NANOBODY®, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a BCMA protein is substantially free of antibodies that specifically bind antigens other than BCMA proteins). An isolated antibody that specifically binds a human BCMA protein may, however, have cross-reactivity to other antigens, such as BCMA proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human BCMA" is intended to refer to an antibody that binds to human BCMA protein (and possibly a BCMA protein from one or more non-human species) but does not substantially bind to non-BCMA proteins. Preferably, the antibody binds to human BCMA protein with "high affinity", namely with a $K_D$ of $5.0\times10^{-8}$ M or less, more preferably $1.0\times10^{-8}$ M or less, and more preferably $7.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $7.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a BIACORE™ system.

The term "antibody-dependent cellular cytotoxicity", "antibody-dependent cell-mediated cytotoxicity" or "ADCC," as used herein, refers to a mechanism of cell-mediated immune defense whereby an effector cell of the immune system actively lyses a target cell, such as a tumor cell, whose membrane-surface antigens have been bound by antibodies such as anti-BCMA antibodies.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

Anti-BCMA Antibodies Having Increased Binding Affinity to Human BCMA and Better Blocking Activity on BCMA-BAFF Binding The antibody, or the antigen-binding portion thereof, of the disclosure specifically binds to human BCMA with comparable, if not better, binding affinity/capacity as compared to previously described anti-BCMA antibodies such as the BCMA binding portion of GSK2857916. The antibody or antigen-binding portion thereof of the disclosure also induces higher antibody dependent cell mediated cytotoxicity (ADCC) at certain concentrations, e.g., at low concentrations, as compared to prior art anti-BCMA antibodies such as the BCMA-binding portion of GSK2857916. When conjugated with a cytotoxin such as DT3C, the antibody or antigen-binding portion thereof of the disclosure is more quickly internalized by cells and shows higher target cell killing activity than prior art anti-BCMA antibodies such as the BCMA-binding portion of GSK2857916.

Additional functional properties include the capacity to block BCMA-BAFF binding.

Preferred antibodies of the disclosure are humanized monoclonal antibodies. Additionally or alternatively, the antibodies can be, for example, chimeric monoclonal antibodies.

Monoclonal Anti-BCMA Antibody

Exemplary antibodies or antigen-binding portions thereof of the disclosure are structurally and chemically characterized as described below. The amino acid sequence ID numbers of the heavy/light chain variable regions and CDRs of the antibodies are summarized in Table 1 below, some antibodies sharing the same $V_H$ or $V_L$. The heavy chain constant region for the antibodies may be human IgG1 heavy chain constant region having an amino acid sequence set forth in, e.g., SEQ ID NO: 12, or a functional fragment thereof, and the light chain constant region for the antibodies may be human kappa constant region having an amino acid sequence set forth in, e.g., SEQ ID NO: 13, or a functional fragment thereof. These antibodies may also contain mouse IgG1 heavy chain constant region, and mouse kappa constant region.

The heavy chain variable region CDRs and the light chain variable region CDRs in Table 1 have been defined by the Kabat numbering system. However, as is well known in the art, CDR regions can also be determined by other systems such as Chothia, IMGT, AbM, and Contact numbering system/method, based on heavy chain/light chain variable region sequences.

The $V_H$ and $V_L$ sequences (or CDR sequences) of other anti-BCMA antibodies which bind to human BCMA can be "mixed and matched" with the $V_H$ and $V_L$ sequences (or CDR sequences) of the anti-BCMA antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another anti-BCMA antibody, wherein the antibody specifically binds human BCMA.

TABLE 1

Amino acid sequence ID numbers of heavy/light chain variable regions

| Antibody | $V_H$ CDR1 | $V_H$ CDR2 | $V_H$ CDR3 | $V_H$ | $V_L$ CDR1 | $V_L$ CDR2 | $V_L$ CDR3 | $V_L$ |
|---|---|---|---|---|---|---|---|---|
| B1H2 | SEQ ID NO.: 1 | SEQ ID NO.: 2 | SEQ ID NO.: 3 | SEQ ID NO.: 7 | SEQ ID NO.: 4 | SEQ ID NO.: 5 | SEQ ID NO.: 6 | SEQ ID NO.: 10 |
| huB1H2-V1 | | | | SEQ ID NO.: 8 | | | | SEQ ID NO.: 11, X1 = T, X2 = V, X3 = Y, X4 = F |
| huB1H2-V2 | | | | SEQ ID NO.: 9, X1 = V, X2 = R, X3 = T | | | | |
| huB1H2-V3 | | | | SEQ ID NO.: 9, X1 = M, X2 = R, X3 = T | | | | |
| huB1H2-V4 | | | | SEQ ID NO.: 9, X1 = V, X2 = S, X3 = T | | | | |
| huB1H2-V5 | | | | SEQ ID NO.: 9, X1 = V, X2 = R, X3 = K | | | | |
| huB1H2-V6 | | | | SEQ ID NO.: 9, X1 = V, X2 = S, X3 = K | | | | |
| huB1H2-V7 | | | | SEQ ID NO.: 8 | | | | SEQ ID NO.: 11, X1 = A, X2 = P, X3 = F, X4 = L |
| huB1H2-V8 | | | | SEQ ID NO.: 9, X1 = V, X2 = R, X3 = T | | | | |
| huB1H2-V9 | | | | SEQ ID NO.: 9, X1 = M, X2 = R, X3 = T | | | | |
| huB1H2-V10 | | | | SEQ ID NO.: 9, X1 = V, X2 = S, X3 = T | | | | |
| huB1H2-V11 | | | | SEQ ID NO.: 9, X1 = V, X2 = R, X3 = K | | | | |
| huB1H2-V12 | | | | SEQ ID NO.: 9, X1 = V, X2 = S, X3 = K | | | | |
| huB1H2-V13 | | | | SEQ ID NO.: 8 | | | | SEQ ID NO.: 11, X1 = A, X2 = V, X3 = F, X4 = L |
| huB1H2-V14 | | | | SEQ ID NO.: 9, X1 = V, X2 = R, X3 = T | | | | |
| huB1H2-V15 | | | | SEQ ID NO.: 9, X1 = M, X2 = R, X3 = T | | | | |
| huB1H2-V16 | | | | SEQ ID NO.: 9, X1 = V, X2 = S, X3 = T | | | | |
| huB1H2-V17 | | | | SEQ ID NO.: 9, X1 = V, X2 = R, X3 = K | | | | |
| huB1H2-V18 | | | | SEQ ID NO.: 9, X1 = V, X2 = S, X3 = K | | | | |
| huB1H2-V19 | | | | SEQ ID NO.: 8 | | | | SEQ ID NO.: 11, X1 = A, X2 = P, X3 = Y, X4 = L |
| huB1H2-V20 | | | | SEQ ID NO.: 9, X1 = V, X2 = R, X3 = T | | | | |
| huB1H2-V21 | | | | SEQ ID NO.: 9, X1 = M, X2 = R, X3 = T | | | | |
| huB1H2-V22 | | | | SEQ ID NO.: 9, X1 = V, X2 = S, X3 = T | | | | |
| huB1H2-V23 | | | | SEQ ID NO.: 9, X1 = V, X2 = R, X3 = K | | | | |
| huB1H2-V24 | | | | SEQ ID NO.: 9, X1 = V, X2 = S, X3 = K | | | | |
| huB1H2-V33 | | | | SEQ ID NO.: 9, X1 = V, X2 = S, X3 = T | | | | SEQ ID NO.: 11, X1 = A, X2 = P, X3 = F, X4 = F |

In another embodiment, an antibody of the disclosure, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-BCMA antibody, wherein the antibody specifically binds human BCMA.

In yet another embodiment, the antibody, or antigen binding portion thereof, includes the heavy chain variable CDR2 region of anti-BCMA antibody combined with CDRs of other antibodies which bind human BCMA, e.g., CDR1 and/or CDR3 from the heavy chain variable region, and/or CDR1, CDR2, and/or CDR3 from the light chain variable region of a different anti-BCMA antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: Scientific Review 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); *Polymenis and Stoller, J. Immunol.* 152: 5218-5329 (1994) and Xu and Davis, *Immunity* 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-BCMA antibody and at least the CDR3 of the heavy and/or light chain variable region of the anti-BCMA antibody, or the CDR3 of the heavy and/or light chain variable region of another anti-BCMA antibody, wherein the antibody is capable of specifically binding to human BCMA. These antibodies preferably (a) compete for binding with BCMA; (b) retain the functional characteristics; (c) bind to the same epitope; and/or (d) have a similar binding affinity as the anti-BCMA antibody of the present disclosure. In yet another embodiment, the antibodies further may comprise the CDR2 of the light chain variable region of the anti-BCMA antibody, or the CDR2 of the light chain variable region of another anti-BCMA antibody, wherein the antibody is capable of specifically binding to human BCMA. In another embodiment, the antibodies of the disclosure may include the CDR1 of the heavy and/or light chain variable region of the anti-BCMA antibody, or the CDR1 of the heavy and/or light chain variable region of another anti-BCMA antibody, wherein the antibody is capable of specifically binding to human BCMA.

Conservative Modifications

In another embodiment, an antibody of the disclosure comprises a heavy and/or light chain variable region sequences of CDR1, CDR2 and CDR3 sequences which differ from those of the anti-BCMA antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or
(d) the light chain variable region CDR1, and/or CDR2, and/or CDR3 sequences comprise the sequence(s) listed in Table 1 above; and/or conservative modifications thereof; and
(e) the antibody specifically binds human BCMA.

The antibody of the present disclosure possesses one or more of the following functional properties described above, such as high affinity binding to human BCMA, and the ability to induce ADCC or CDC against BCMA-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered and Modified Antibodies

Antibodies of the disclosure can be prepared using an antibody having one or more of the $V_H$/$V_L$ sequences of the anti-BCMA antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad. See also U.S.A.* 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG--0010109, NT--024637 & BC070333), 3-33 (NG--0010109 & NT--024637) and 3-7 (NG--0010109 & NT--024637). As another example, the following heavy chain germline sequences found in the HCo12 HuMAb mouse are available in the accompanying Genbank Accession Nos.: 1-69 (NG--0010109, NT--024637 & BC070333), 5-51 (NG--0010109 & NT--024637), 4-34 (NG--0010109 & NT--024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-BCMA monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypo fucosylated antibody having reduced amounts of fucosyl residues or an antibody having increased bisecting GlcNac structures. Such altered glycosylation patterns have been demonstrated to increase the ADCC ability of antibodies.

Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (a (1, 6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn (297)-linked carbohydrates, also resulting in hypofucosylation of antibodies expressed in that host cell (see also Shields et al., (2002) *J. Biol. Chem.* 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application No. 60/836,998, filed on Aug. 11, 2006. PCT Publication WO 99/54342 describes cell lines engineered to express glycoprotein-modifying glycosyl transferases (e.g., β (1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibody's Physical Properties

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12: 43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-BCMA antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The de-amidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-BCMA antibody that contains a pI value that falls in the normal range. This can be achieved either by selecting antibodies with a pI in the normal range or by mutating charged surface residues.

Production of Monoclonal Antibodies of the Disclosure

Monoclonal antibodies (mAbs) of the present disclosure can be produced using the well-known somatic cell hybridization (hybridoma) technique of Kohler and Milstein (1975) *Nature* 256:495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Disclosure

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe et al., (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the disclosure can be conjugated to a therapeutic agent to form an immunoconjugate such as an antibody-drug conjugate (ADC). Suitable therapeutic agents include cytotoxins such as DT3C, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-BCMA binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity.

At the other extreme are bispecific molecules consisting of two single-chain antibody fragments (scFv's) linked by a peptide chain, a so-called Bs (scFv) 2 construct. Intermediate-sized bispecific molecules include two different F (ab) fragments linked by a peptidyl linker. Bispecific molecules of these and other formats can be prepared by genetic engineering, somatic hybridization, or chemical methods. See, e.g., Kufer et al, cited supra; Cao and Suresh, Bioconjugate Chemistry, 9 (6), 635-644 (1998); and van Spriel et al., *Immunology Today,* 21 (8), 391-397 (2000), and the references cited therein.

Antibody-Encoding or Antibody-Bearing Oncolytic Virus

An oncolytic virus preferentially infects and kills cancer cells. Antibodies of the present disclosure can be used in conjunction with oncolytic viruses. Alternatively, oncolytic viruses encoding antibodies of the present disclosure can be introduced into human body.

Chimeric Antigen Receptor

Also provided herein are a chimeric antigen receptor (CAR) containing an anti-BCMA scFv, the anti-BCMA scFv comprising CDRs and heavy/light chain variable regions described herein.

The anti-BCMA CAR may comprise (a) an extracellular antigen binding domain comprising an anti-BCMA scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, comprising the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

Nucleic Acid Molecules Encoding Antibodies of the Disclosure

In another aspect, the disclosure provides a nucleic acid molecule that encodes the antibody or antigen-binding portion thereof, the immunoconjugate, the bispecific molecule, or the CAR, of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the BCMA monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Pharmaceutical Compositions

In another aspect, the present disclosure provides a pharmaceutical composition comprising one or more antibodies (or antigen-binding portions thereof, the bispecifics, CAR-T cells, oncolytic viruses, immunoconjugates, nucleic acid molecules, expression vectors or host cells) of the present disclosure formulated together with a pharmaceutically acceptable carrier. The antibodies (or antigen-binding portions thereof, the bispecifics, CAR-T cells, oncolytic viruses, immunoconjugates, nucleic acid molecules, expression vectors or host cells) can be dosed separately when the composition contains more than one antibody (or antigen-binding portion thereof, bispecific, CAR-T cell, oncolytic virus, immunoconjugate, nucleic acid molecule, expression vector or host cell). The composition may optionally contain one or more additional pharmaceutically active ingredients, such as another antibody or a drug, such as an anti-tumor drug.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg. An exemplary treatment regime entails administration once per week.

A "therapeutically effective dosage" of the anti-BCMA antibody or antigen-binding portion thereof, the immunoconjugate, the bispecific molecule, the CAR, the immune cell, the oncolytic virus, the nucleic acid molecule, the expression vector or the host cell of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Disclosure

The pharmaceutical composition of the present disclosure has numerous in vitro and in vivo utilities involving, for example, treatment of tumors associated with increased BCMA expression.

Given the ability of the anti-BCMA antibodies or antigen-binding portions thereof of the disclosure to inhibit proliferation and survival of BCMA-expressing tumor cells, the disclosure provides methods for inhibiting growth of tumor cells in a subject comprising administering to the subject the pharmaceutical composition of the disclosure such that growth of the tumor is inhibited in the subject. Non-limiting examples of tumors that can be treated by antibodies of the disclosure include, but not limited to, such as leukemia, lymphomas and multiple myeloma. Additionally, refractory or recurrent malignancies whose growth may be inhibited using the antibodies of the disclosure.

Combination Therapy

In another aspect, the disclosure provides methods of combination therapy in which the pharmaceutical composition the present disclosure is co-administered with one or more additional antibodies that are effective in inhibiting tumor growth in a subject. In one embodiment, the disclosure provides a method for inhibiting tumor growth in a subject comprising administering to the subject the pharmaceutical composition of the disclosure and one or more additional antibodies, such as an anti-VISTA antibody, an anti-LAG-3 antibody, an anti-PD-L1 antibody, and anti-PD-1 antibody and/or an anti-CTLA-4 antibody. In certain embodiments, the subject is human.

The BCMA signaling activation can also be further combined with standard cancer treatments. For example, BCMA signaling activation a can be combined with CTLA-4 and/or LAG-3 and/or PD-1 blockade and also chemotherapeutic regimes. For example, a chemotherapeutic agent can be administered with the anti-BCMA antibodies, which may be a cytotoxic agent. For example, epirubicin, oxaliplatin, and 5-FU are administered to patients receiving anti-BCMA therapy.

Optionally, the combination of the pharmaceutical composition of the disclosure and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

Other therapies that may be combined with the anti-BCMA therapy includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-BCMA Monoclonal Antibodies Using Hybridoma Technology Immunization Mice were immunized according to the method as described in E Harlow, D. Lane, Antibody: A Laboratory Manual, Cold Spring Harbor Laboratory Press, Cold Spring Harbor, N.Y., 1998. Recombinant human BCMA protein with Fc tag at the C-terminus (Cat #BC7-H5254, ACRO BIOSYSTEMS™) was used as the immunogen. Human BCMA-his protein (Cat #BCA-H522Y, ACRO BIOSYSTEMS™) was used for determining anti-sera titer and for screening hybridomas secreting antigen-specific antibodies. Immunizing dosages contained 25 μg human BCMA-Fc protein/mouse/injection for both primary and boost immunizations. To increase immune response, the complete Freud's adjuvant and incomplete Freud's adjuvant (Sigma, St. Louis, Mo., USA) were used respectively for primary and boost immunizations. Briefly, adjuvant-antigen mixture was prepared by first gently mixing the adjuvant in a vial using a vortex. The desired amount of adjuvant was transferred to an autoclaved 1.5 mL micro-centrifuge tube. The antigen was prepared in PBS or saline with concentrations ranging from 0.25 to 0.34 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into proper syringes for animal injection. A total of 25 μg antigen was injected in a volume of 150-200 μl. Each animal was immunized, and then boosted for 2 to 3 times depending on the anti-sera titer. Animals with good titers were given a final boost by intraperitoneal injection before fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with myeloma cells according to the method as described in Kohler G, and Milstein C, "Continuous cultures of fused cells secreting antibody of predefined specificity," Nature, 256:495-497 (1975). Fused "hybrid cells" were subsequently dispensed into 96-well plates in DMEM/20% FCS/HAT media. Surviving hybridoma colonies were observed under the microscope seven to ten days post fusion. After two weeks, the supernatant from each well was subjected to Capture ELISA using biotin-labeled human BCMA-his protein. Positive hybridoma secreting antibodies that bound to human BCMA-his proteins were then selected and transferred to 24-well plates. These hybridomas were further tested for human BAFF-BCMA blocking activities. Hybridoma clones producing antibodies that showed high specific human BCMA binding and BCMA-BAFF blocking activities were subcloned by limiting dilution to ensure the clonality of the cell line, and then monoclonal antibodies were purified. Briefly, Protein A sepharose column (from bestchrom (Shanghai) Biosciences, Cat #AA0273) was washed using PBS buffer in 5 to 10 column volumes. Cell supernatants were then passed through the columns, and the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C. Subsequently, the in vitro functional activities of purified monoclonal antibodies were characterized as follows.

Example 2 Affinity Determination of Mouse Anti-BCMA Monoclonal Antibody Using BIACORE™ Surface Plasmon Resonance Technology The purified anti-BCMA mouse monoclonal antibody B1H2 (mAb) generated in Example 1 was characterized for affinity and binding kinetics by BIACORE™ T200 system (GE HEALTHCARE™, Pittsburgh, PA, USA).

Briefly, goat anti-mouse IgG (GE HEALTHCARE™, Cat #BR100838, Mouse Antibody Capture Kit) was covalently linked to a CM5 chip (carboxy methyl dextran coated chip) via primary amines using a standard amine coupling kit provided by BIACORE™ (GE HEALTHCARE™, Pittsburgh, PA, USA). Un-reacted moieties on the biosensor surface were blocked with ethanolamine. A Protein G chip (GE HEALTHCARE™, Cat #29-1793-15) was used for the affinity determination of the positive control, i.e., a full-length antibody containing BCMA-binding portion of GSK2857916, also referred to as BCMA BM1 or BM, prepared in house using the heavy chain and light chain amino acids set forth in SEQ ID NOs.: 14 and 15. The purified mouse anti-BCMA antibodies and the positive controls at the concentration of 2 μg/mL, were flowed onto the chip at a flow rate of 10 μL/min. Then, serially diluted recombinant human BCMA-his (ACRO BIOSYSTEMS™, Cat #BCA-H522Y) or cynomolgus monkey BCMA-Fc protein (ACRO BIOSYSTEMS™, Cat #BCA-C5253), 2-fold dilution in HBS-$EP^{+}$ buffer (provided by BIACORE™) starting at 10 nM, were flowed onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BIACORE™ evaluation software. The $K_D$, $K_a$ and $K_d$ values were determined and summarized in Table 2 below.

10000 ng/ml, respectively, for 40 minutes at 37° C., and then washed 4 times again. Plates containing the captured anti-BCMA antibodies were incubated with biotin-labeled human BCMA-his protein (Cat #BCA-H522Y, ACRO BIOSYSTEMS™, 4.125 ng/ml in 2.5% non-fatty milk in PBST, 100 μl/well) for 40 minutes at 37° C., washed 4 times, and incubated with streptavidin conjugated HRP (1:10000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002). The reaction was stopped in 3-10 minutes at room temperature with 50 μl/well 1M $H_2SO_4$, and the absorbance of each well was read on a microplate reader using dual wavelengths mode with 450 nm for TMB and 630 nm as the reference wavelength. The OD (450-630) values were plotted against antibody concentration. Data were analyzed using Graphpad Prism software and $EC_{50}$ values were reported. The results were shown in FIG. 1

3.2 Cell Based Binding FACS

Binding of anti-BCMA antibody B1H2 to the surface of U266 Cells was tested by flow cytometry (FACS). Briefly, human myeloma cells U266 (ATCC® TIB-196™) were harvested from cell culture flasks, washed twice and re-suspended in phosphate buffered saline (PBS) containing 2% v/v Fetal Bovine Serum (FACS buffer). $2\times10^5$ cells per well in 96 well-plates were incubated with 100 μl serially diluted anti-BCMA antibodies or controls (starting from 10 μg/mL, 5-fold serial dilution) in FACS buffer for 40 minutes

TABLE 2

Binding affinity of mouse anti-BCMA antibody B1H2 to human BCMA and cynomolgus BCMA

| | Kinetics on BIACORE ™ | | | | | |
|---|---|---|---|---|---|---|
| | Human BCMA-his | | | Cynomolgus BCMA-Fc | | |
| Mouse mAb | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| B1H2 | 5.42E+06 | 1.10E−03 | 2.03E−10 | No binding | No binding | No binding |
| BCMA BM1 | 3.30E+05 | 2.45E−04 | 7.42E−10 | not tested | not tested | not tested |

The mouse antibody B1H2 specifically bound to human BCMA with higher binding affinity than the benchmark, but did not bind to monkey BCMA.

Example 3 Binding Activities of Mouse Anti-BCMA Monoclonal Antibody

The binding activities of mouse anti-BCMA antibody B1H2 to human BCMA were determined by Capture ELISA, Indirect ELISA and Flow Cytometry (FACS).

3.1 Capture ELISA

Figure 2:
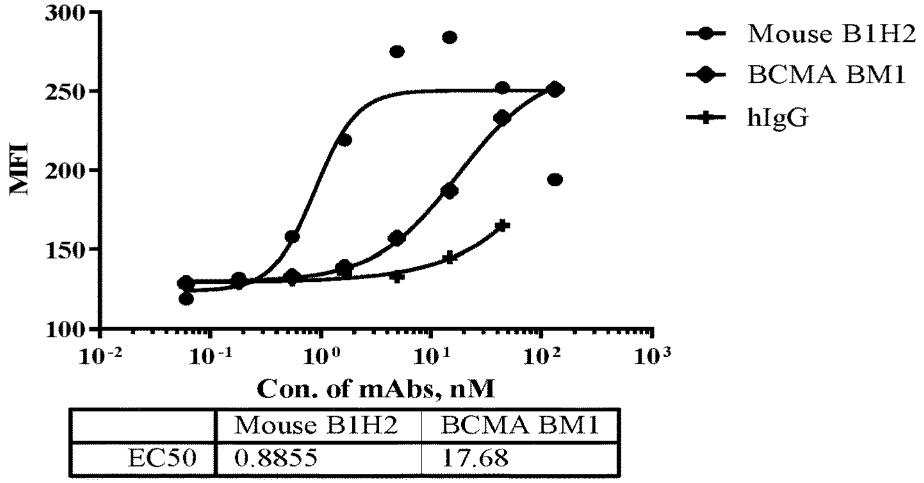
FIG. 2 shows the binding capacity of mouse B1H2 antibody to U266 cells expressing human BCMA in a cell based binding FACS assay.

Briefly, 96-well micro plates were coated with 2 μg/ml goat anti-mouse IgG Fcγ fragment specific (Jackson Immuno Research, Cat #115-005-071) in PBS, 100 μl/well, and incubated overnight at 4° C. Plates were washed once with wash buffer (PBS+0.05% Tween-20, PBST) and then blocked with 200 μl/well blocking buffer (5% w/v non-fatty milk in PBST) for 2 hours at 37° C. Plates were washed again and incubated with 100 μl/well serially diluted purified mouse anti-BCMA B1H2 antibodies, the benchmark and negative control hIgG (human immunoglobulin (pH4) for intravenous injection, Hualan Biological Engineering Inc.), 5-fold dilution in 2.5% non-fatty milk in PBST starting at on ice. Cells were washed twice with FACS and buffer, added with 100 μL/well. R-Phycoerythrin AffiniPure $F(ab')_2$ Fragment Goat Anti-Mouse IgG (H+L) (1:1000 dilution in FACS buffer, Jackson Immunoresearch, Cat #115-116-146). Following an incubation for 40 minutes at 4° C. in dark, cells were washed three times and re-suspended in FACS buffer. Fluorescence was measured using a Becton Dickinson FACS Canto II-HTS equipment, and the MFI (mean fluorescence intensity) was plotted against antibody concentration. Data were analyzed using Graphpad Prism software and $EC_{50}$ values were reported as the antibody concentration to achieve 50% of maximal anti-BCMA binding to U266 cells. The results were shown in FIG. 2.

The results indicated that the mouse anti-BCMA antibody B1H2 specifically bound to human BCMA. In FIG. 1, the B1H2 had lower $EC_{50}$ than the positive control in the Capture ELISA. According to FIG. 2, the mouse anti-BCMA antibody B1H2 of the disclosure bound to human BCMA on the cell surface with lower $EC_{50}$ and higher Bmax than the benchmark. The data suggested that the B1H2 antibody had better BCMA binding capacity.

Example 4 Competitive ELISA of Mouse Anti-BCMA Monoclonal Antibody 4.1 Ligand Blocking ELISA The ability of anti-BCMA antibody B1H2 of the disclosure to block BCMA-BAFF binding was measured in a competitive ELISA assay. Briefly, 100 μl human BCMA-his protein (ACRO BIOSYSTEMS™, Cat #BCA-H522Y) were coated on 96-well micro plates at 2 μg/mL in carbonate/bicarbonate buffer for 2 hours at 37° C. Plates were washed with wash buffer (PBS+0.05% w/v Tween-20, PBST), and blocked with 5% w/v non-fatty milk in PBST for 2 hours at 37° C. Plates were then washed again using wash buffer.

Serially diluted anti-BCMA B1H2 antibodies or controls (starting at 200 nM with a four-fold serial dilution) in PBST with 2.5% w/v non-fatty milk were added to the BCMA-his bound plates, 100 μl per well, and incubated with the human BCMA-his protein at 37° C. for 40 minutes. Plates were washed 4 times using wash buffer, and then 100 μl/well of 10.5 ng/ml biotin-labeled BAFF-Fc protein (Sino biological inc., Cat #10056-H01H) was added and incubated for 40 minutes at 37° C. Plates were washed again using wash buffer. Thereafter, the plates were added with 100 μl/well streptavidin conjugated HRP (1:5000 dilution in PBST buffer, Jackson Immunoresearch, Cat #016-030-084) and incubated for 40 minutes at 37° C. Plates were washed again using wash buffer. Finally, TMB was added and the reaction was stopped using 1M $H_2SO_4$. The absorbance of each well was read on a microplate reader using dual wavelengths mode with 450 nm for TMB and 630 nm as the reference wavelength, then the OD (450-630) values were plotted against antibody concentration. Data were analyzed using Graphpad Prism software and $IC_{50}$ values were reported.

4.2 Benchmark Blocking ELISA

The ability of the anti-BCMA antibody B1H2 of the disclosure to block benchmark-human BCMA binding was measured using a competitive ELISA assay. Briefly, the BCMA BM1 was coated on 96-well micro plates at 2 μg/mL in PBS, 100 μl per well, and incubated for 2 hours at 37° C. Then plates were washed with wash buffer, and blocked with 5% w/v non-fatty milk in PBST for 2 hours at 37° C. While blocking, anti-BCMA antibodies of the disclosure or controls were diluted with biotin labeled human BCMA-his proteins (ACRO BIOSYSTEMS™, Cat #BCA-H522Y, 3.3 ng/mL in PBST with 2.5% non-fatty milk), starting at 100 nM with a 4-fold serial dilution, and incubated at room temperature for 40 minutes. After plate washing, the antibody/biotin labeled human BCMA-his mixtures were added to BCMA BM1 coated plates, 100 μl per well. After incubation at 37° C. for 40 minutes, plates were washed using wash buffer. Then the plates were added and incubated with 100 μl/well streptavidin conjugated HRP for 40 minutes at 37° C. Plates were washed again using wash buffer. Finally, TMB was added and the reaction was stopped using 1M $H_2SO_4$. The absorbance of each well was read on a microplate reader using dual wavelengths mode with 450 nm for TMB and 630 nm as the reference wavelength, then the OD (450-630) values were plotted against antibody concentration. Data were analyzed using Graphpad Prism software and $IC_{50}$ values were reported.

Figure 3:
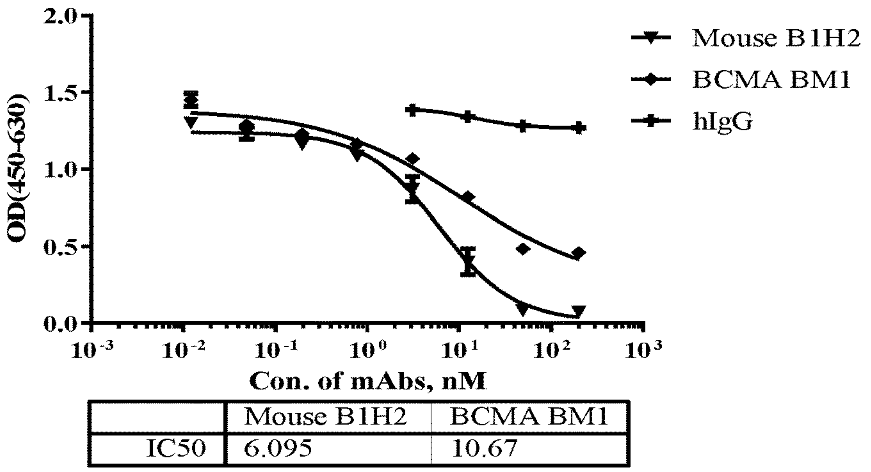
FIG. 3 shows the blocking ability of mouse antibody B1H2 on human BCMA-BAFF binding in a competitive ELISA.
Figure 4:
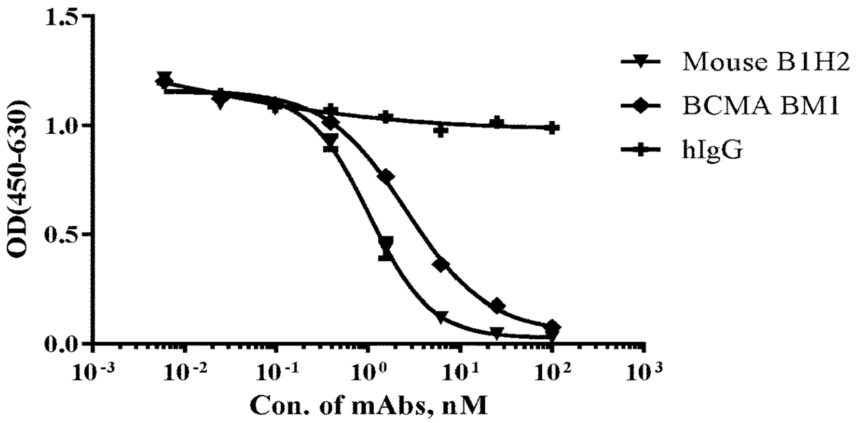
FIG. 4 shows the blocking ability of mouse antibody B1H2 on benchmark-human BCMA binding in a competitive ELISA test.

The results of the two assays were summarized in FIGS. 3 and 4.

It can be seen from FIG. 3 that the anti-BCMA antibody B1H2 was capable of blocking human BCMA binding to BAFF, with a bit higher blocking activity than BCMA BM1.

FIG. 4 showed that the antibody B1H2 was able to block human BCMA-BM1 binding, suggesting that it bound to the same or similar epitope as BCMA BM1 did.

Example 5 Generation of Chimeric Antibody

The variable domains of the heavy and light chain of the anti-BCMA mouse mAb B1H2 were sequenced, and the sequence ID numbers were summarized in Table 1.

The variable domains of the heavy and light chains were cloned in frame to human IgG1 heavy-chain (SEQ ID NO.: 12) and human kappa light-chain constant regions (SEQ ID NO.: 13), respectively, wherein the C terminus of variable region was linked to the N terminus of the respective constant region.

The vectors each containing a nucleotide encoding a heavy chain variable region linked to human IgG1 heavy-chain constant region, and the vectors each containing a nucleotide encoding a light chain variable region linked to human kappa light-chain constant region were transiently transfected into 50 ml of 293F suspension cell cultures in a ratio of 1.1:1 light to heavy chain construct, with 1 mg/mL PEI.

Cell supernatant was harvested after six days in shaking flasks, spun down to pellet cells, and then chimeric antibodies were purified from the cell supernatant.

Example 6 Humanization of Anti-BCMA Mouse Monoclonal Antibody B1H2

Mouse anti-BCMA antibody B1H2 was humanized and further characterized. Humanization of this mouse antibody was conducted using the well-established CDR-grafting method as described in detail below.

To select acceptor frameworks for humanization of mouse antibody B1H2, the light and heavy chain variable region sequences of this mouse antibody B1H2 were blasted against the human immunoglobulin gene database. The human germlines with the highest homology were selected as the acceptor frameworks for humanization. The mouse antibody heavy/light chain variable region CDRs were inserted into the selected frameworks, and the residue(s) in the frameworks was/were further mutated to obtain more candidate heavy chain/light chain variable regions. A total of 25 humanized B1H2 antibodies (namely from huB1H2-V1 to huB1H2-V24 and huB1H2-V33) were obtained whose heavy/light chain variable region sequences were in Table 1.

The vectors each containing a nucleotide encoding humanized B1H2 heavy chain variable regions linked to human IgG1 heavy-chain constant region (SEQ ID NO: 12), and the vectors each containing a nucleotide encoding humanized B1H2 light chain variable region linked to human kappa light-chain constant region (SEQ ID NO: 13) were transiently transfected into 50 ml of 293F suspension cell cultures in a ratio of 60% to 40% light to heavy chain construct, with 1 mg/ml PEI.

Example 7 Characterization of Humanized B1H2 Antibodies

Cell supernatants containing humanized antibodies were harvested after six days in shaking flasks and tested for binding affinity to human BCMA by Octect following the protocol described below.

The Octet affinity test was performed using Octet® system (Fortebio, Octet RED 96). Briefly, AHC biosensors (anti-human IgG Fc capture, from ForteBio) were presoaked with 10 mM glycine (pH 1.5) for 3 seconds, and then dipped in a well with running buffer (0.5% w/v BSA in PBST) for 3 seconds, the soaking and dipping steps were repeated for three times. Then, the sensors were dipped in a well with the cell supernatants containing humanized antibodies, the chimeric B1H2 antibody in HBS-$EP^+$ at 10 μg/ml, or the BCMA BM1 in HBS-$EP^+$ at 10 μg/ml for 100 seconds, and then immersed in a well with running buffer for 5 min. A new baseline was run for 180 seconds in another well with running buffer. Then the sensors were dipped in a well with diluted human BCMA-his protein (ACRO BIOSYSTEMS™, Cat #BCA-H522Y, starting at 80 nM with a two-fold serial dilution) in running buffer for 100 seconds, and then immersed in a baseline well for 10 min. Finally, sensors were presoaked with 10 mM glycine (pH 1.5) for 3 seconds, and then were dipped in a well with running buffer for 3 seconds, the soaking and dipping steps were repeated for three times. The association and dissociation curves were fit to a 1:1 Langmuir binding model using ForteBio Data Analysis 8.1 evaluation software. The $K_a$, $K_d$ and $K_D$ values were determined and summarized in Table 3 below.

The data indicated that the humanized antibodies as tested, such as huB1H2-V1 to huB1H2-V7, huB1H2-V12 and huB1H2-V33, exhibited high and comparable binding affinity as compared with chimeric B1H2 antibody.

TABLE 3

Affinities of Humanized B1H2 mAbs
Octet Kinetics of Humanized B1H2 mAbs Binding to Human BCMA

| mAb | Kinetics on Octet Human BCMA-his $K_a$ ($M^{-1}s^{-1}$) | $K_d$ ($s^{-1}$) | $K_D$ (M) |
|---|---|---|---|
| huB1H2-V1 | 4.07E+05 | 4.98E−04 | 1.22E−09 |
| huB1H2-V2 | 5.73E+05 | 7.42E−04 | 1.29E−09 |
| huB1H2-V3 | 5.50E+05 | 4.02E−04 | 7.31E−10 |
| huB1H2-V4 | 1.08E+06 | 2.90E−04 | 2.69E−10 |
| huB1H2-V5 | 4.07E+05 | 3.72E−04 | 9.15E−10 |
| huB1H2-V6 | 3.92E+05 | 4.40E−04 | 1.12E−09 |
| huB1H2-V7 | 6.71E+05 | 4.34E−04 | 6.47E−10 |
| huB1H2-V8 | 5.10E+05 | 1.34E−03 | 2.62E−09 |
| huB1H2-V9 | 3.21E+05 | 1.51E−03 | 4.71E−09 |
| huB1H2-V10 | 3.63E+05 | 7.33E−04 | 2.02E−09 |
| huB1H2-V11 | 3.98E+05 | 2.16E−03 | 5.43E−09 |
| huB1H2-V12 | 4.53E+05 | 7.91E−04 | 1.75E−09 |
| huB1H2-V13 | 3.12E+05 | 6.88E−04 | 2.21E−09 |
| huB1H2-V14 | 2.66E+05 | 1.37E−03 | 5.14E−09 |
| huB1H2-V15 | 2.26E+05 | 1.37E−03 | 6.06E−09 |
| huB1H2-V16 | 2.54E+05 | 8.87E−04 | 3.50E−09 |
| huB1H2-V17 | 2.60E+05 | 2.38E−03 | 9.16E−09 |
| huB1H2-V18 | 4.15E+05 | 9.21E−04 | 2.22E−09 |
| huB1H2-V19 | 2.44E+05 | 6.47E−04 | 2.65E−09 |
| huB1H2-V20 | 2.34E+05 | 1.41E−03 | 6.00E−09 |
| huB1H2-V21 | 1.99E+05 | 1.42E−03 | 7.12E−09 |
| huB1H2-V22 | 2.29E+05 | 8.62E−04 | 3.77E−09 |
| huB1H2-V23 | 1.05E+05 | 2.14E−03 | 2.04E−08 |
| huB1H2-V24 | 1.64E+05 | 1.00E−03 | 6.10E−09 |
| huB1H2-V33 | 9.76E+06 | 0.003409 | 3.49E−10 |
| Chimeric B1H2 | 6.61E+05 | 4.45E−04 | 6.73E−10 |
| BCMA BM1 | 2.86E+05 | 1.25E−04 | 4.36E−10 |

The humanized antibodies huB1H2-V10 and huB1H2-V33 were purified as described above and tested in BIACORE™, Capture ELISA, Indirect ELISA, Protein thermal shift assay, Cell-based binding FACS, Competitive ELISA, Internalization-mediated cellular toxicities and Antibody-dependent cell-mediated cytotoxicity (ADCC) assay, following the protocols in the foregoing Examples with minor modifications and protocols described below.

For the BIACORE™ assay, goat anti-human IgG (GE HEALTHCARE™, Cat #BR100839, Human Antibody Capture Kit) was covalently linked to a CM5 chip instead of goat anti-mouse IgG, and a CM5 chip was used for the benchmark instead of the Protein G chip. The results were shown in Table 5.

For the Capture ELISA, AffiniPure Goat Anti-Human IgG, Fcγ fragment specific (Jackson Immunoresearch, Cat #109-005-098) was used instead of AffiniPure Goat Anti-Mouse IgG, Fcγ fragment specific, 100 μl/well. The results were shown in FIG. 5.

The indirect ELISA for testing the antibodies' binding capacities to cynomolgus monkey BCMA protein was performed as follows. Briefly, 96-well micro plates were coated with 100 μl 2 μg/ml cynomolgus BCMA-his protein (ACRO BIOSYSTEMS™, Cat #BCA-C52H7) in PBS for 2 hours at 37° C. Plates were washed once with wash buffer (PBS+0.05% Tween-20, PBST) and then blocked with 200 μl/well blocking buffer (5% w/v non-fatty milk in PBST) for 2 hours at 37° C. Plates were washed again and incubated with 100 μl/well serially diluted anti-BCMA antibodies of the disclosure, the BCMA BM1 or negative control hIgG (human immunoglobulin (pH4) for intravenous injection, Hualan Biological Engineering Inc.) (5-fold dilution in PBST with 2.5% non-fatty milk, starting at 10000 ng/ml) for 40 minutes at 37° C. ELISA plates were washed 4 times and incubated with Peroxidase AffiniPure $F(ab')_2$ Fragment Goat Anti-Human IgG, Fcγ Fragment Specific (1:5000 dilution in PBST buffer, Jackson Immunoresearch, Cat #109-036-098, 100 μl/well) for 40 minutes at 37° C. After a final wash, plates were incubated with 100 μl/well TMB (Innoreagents). The reactions were stopped 3-10 minutes later at room temperature with 50 μl/well 1M $H2SO_4$, and the absorbance of each well was read on a microplate reader using dual wavelength mode with 450 nm for TMB and 630 nm as the reference wavelength. The OD (450-630) values were plotted against antibody concentration. Data were analyzed using Graphpad Prism software and $EC_{50}$ values were reported. The results were shown in FIG. 6.

In the cell-based binding FACS, Biosion in-house prepared 293F-BCMA cells stably expressing human BCMA (SEQ ID NO.: 16, amino acid residues 1-184 of uniprot #Q02223) were used instead of U266 cells, $2\times10^5$ cells/well, wherein the 293F-BCMA cells were prepared by transfecting 293F cells (Thermofisher Inc., Cat #11625019) with a pcDNA3.1 plasmid inserted with BCMA (SEQ ID NO:16) coding sequence between NotI and XbaI sites, following the instruction of lipofectamine 3000 transfection reagent (Thermo Fisher). R-Phycoerythrin AffiniPure Goat Anti-Human IgG, Fcγ fragment specific, Jackson Immunoresearch, Cat #109-115-098) was used instead of R-Phycoerythrin AffiniPure $F(ab')_2$ Fragment Goat Anti-Mouse IgG (H+L), 100 μl/well. The results were shown in FIG. 7. For the thermal shift assay, a protein thermal shift assay was used to determine melting temperature (Tm) using a GloMelt™ Thermal Shift Protein Stability Kit (Biotium, Cat #33022-T). Briefly, the GloMelt™ dye was allowed to thaw and reach room temperature. The vial containing the dye was vortexed and centrifuged. Then, 10× dye was prepared by adding 5 μL 200× dye to 95 μL PBS. 2 μL 10× dye was added with 10 μg humanized antibodies, and PBS was added to a total reaction volume of 20 μL. The tubes containing the dye and antibodies were briefly spun and placed in real-time PCR thermocycler (Roche, LightCycler 480 II) set up with a melt curve program having the parameters in Table 4. The results were shown in FIGS. 12A and 12B.

TABLE 4

| Parameters for Melt Curve Program | | | |
|---|---|---|---|
| Profile step | Temperature | Ramp rate | Holding Time |
| Initial hold | 25° C. | NA | 30 s |
| Melt curve | 25-99° C. | 0.1° C./s | NA |

The ADCC activities induced by anti-BCMA humanized antibodies were tested using a luciferase detection system (Bio-Lite™ Luciferase Assay system, Promega, Cat #E6120). Jurkat-NFAT-CD16a stable cell line (clone ID #2B1-1D2), as the effector cell line, stably expressing CD16a on cell membrane was in house made by transfecting Jurkat cells with pGL4.30 plasmids (Promega, Cat #pGL4.30 [luc2P/NFAT-RE/Hygro) which contained an NFAT response element (NFAT-RE) driving transcription of the luciferase reporter gene luc2P (Photinus pyralis) and pUNO1-hFCGR3Ac plasmids (Invivogene, Cat #pUNO1-hFCGR3Ac), following the instruction of lipofectamine 3000 transfection reagent (Thermo Fisher). Specifically, $1.25\times10^4$ cells U266 cells as the target cells in 100 μL RPMI1640 medium (Gibco, Cat #A10491-01) supplemented with 10% FBS (Gibco, Cat #10099-141) were seeded into 96-well plates, and incubated with 50 μl anti-BCMA antibodies at various concentrations (133.33 nM, 66.67 nM, 6.67 nM, 0.67 nM, 0.07 nM, 0.01 nM, 0.001 nM, 0.0001 nM, 0.00001 nM and 0.0 nM) for 1 hour in a $CO_2$ incubator at 37° C. Then, the plates were added with $7.5\times10^4$ effector cells in 50 μL RPMI1640 medium supplemented with 10% FBS and mixed with target cells at an E/T ratio of 6:1. The mixtures were incubated for 6 hours at 37° C. in a humidified atmosphere casing with 5% $CO_2$. Then, 100 μl supernatant was discarded per well. The plates were added and incubated with Luciferase detection Reagent (50 μL/well, Promega, Cat #E6120) for 10 minutes later, and analyzed by Tecan infinite 200Pro plate-reader. Data of luminescence signal were analyzed using Graphpad prism software and $EC_{50}$ values were reported. The results were shown in FIGS. 10A and 10B.

In the cell-based internalization assay, the anti-BCMA humanized antibodies were evaluated precisely for their internalization efficiency in U266 cells (ATCCR TIB-196). Firstly a recombinant protein termed DT3C was synthesized, which consisted of diphtheria toxin (DT) lacking the receptor-binding domain and the C1, C2, and C3 domains of *Streptococcus* protein G (3C) (prepared in house, SEQ ID NO: 23). Then, $1.5\times10^4$ U266 cells in 100 μL RPMI1640 medium (Gibco, Cat #A10491-01) supplemented with 10% FBS (Gibco, Cat #10099-141) were plated onto each well of 96 well-plates (Corning, Cat #3903). Meanwhile, the anti-BCMA antibodies of the disclosure or controls, 40 μg/mL in RPMI1640 medium with 10% FBS, were mixed with DT3C proteins, 40 μg/mL in RPMI1640 medium with 10% FBS, at 1:1 volume ratio, and incubated at room temperature for 30 minutes. Then, 100 μl of serially diluted antibody/DT3C mixtures (starting from 20 μg/mL, 3-fold serial dilution in the culture medium) were added to the cell plates, and incubated in a $CO_2$ incubator at 37° C. for 72 hours. The plates were added with Cell Titer Glo reagent (Promega, Cat #G7570) and incubated for 10 minutes. The cell culture plates were then analyzed by Tecan infinite 200Pro plate-reader. Data were analyzed using Graphpad prism software and $IC_{50}$ values were reported as the antibody concentrations that achieved 50% of maximal inhibition on cell viability. When the mAb-DT3C conjugates were internalized by the target cells, target cell viability markedly decreased. If the conjugates were not internalized, then the free DT3Cs had no or little cell killing activity. The data were shown in FIG. 11 and Table 6. The results of other assays were shown in FIGS. 8 and 9.

TABLE 5

| Binding affinities of humanized mAbs | | | |
|---|---|---|---|
| | Kinetics on BIACORE ™ Human BCMA-his | | |
| mAb ID# | Ka ($M^{-1}s^{-1}$) | $K_d$ ($s^{-1}$) | $K_D$ (M) |
| Mouse B1H2 | 1.03E+07 | 7.83E−04 | 7.57E−11 |
| Chimeric B1H2 | 7.85E+06 | 6.58E−04 | 8.39E−11 |
| huB1H2-V33 | 9.76E+06 | 0.003409 | 3.49E−10 |
| huB1H2-V10 | 2.73E+07 | 0.007882 | 2.89E−10 |
| BCMA BM1 | 2.44E+05 | 1.41E−04 | 5.78E−10 |

Figure 5:
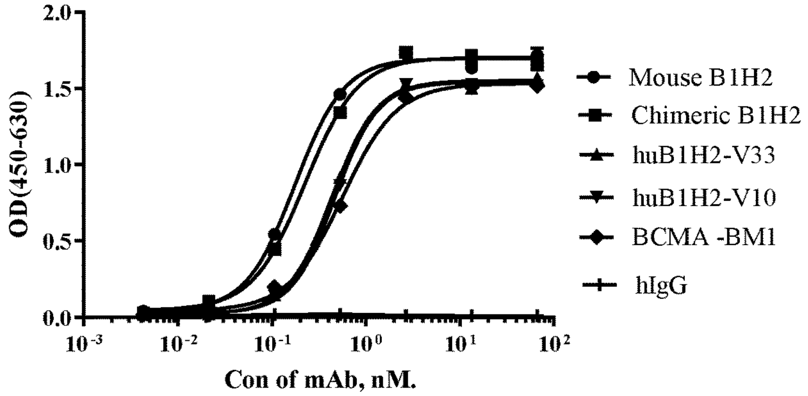
FIG. 5 shows the binding capacities of chimeric and humanized B1H2 antibodies to human BCMA in a capture ELISA.
Figure 7:
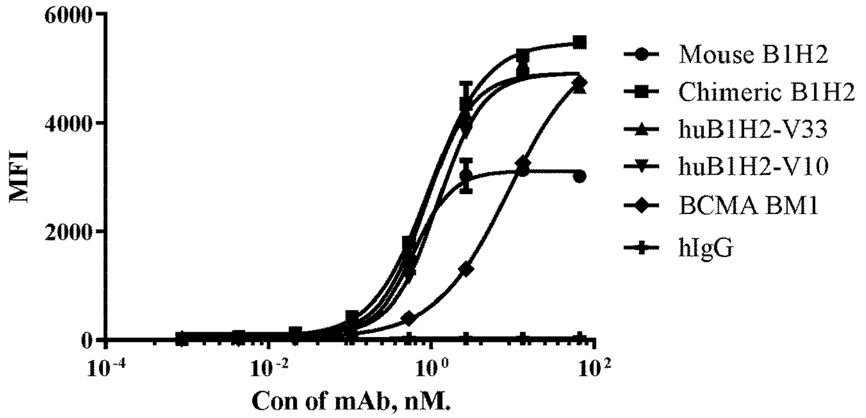
FIG. 7 shows the binding capacities of chimeric and humanized B1H2 antibodies to 293F cells expressing human BCMA in a cell based binding FACS assay.

It can be seen from Table 5 and FIGS. 5 and 7 that mouse, chimeric and humanized B1H2 antibodies exhibited higher binding affinities/capacities as compared with BCMA BM1.

Figure 6:
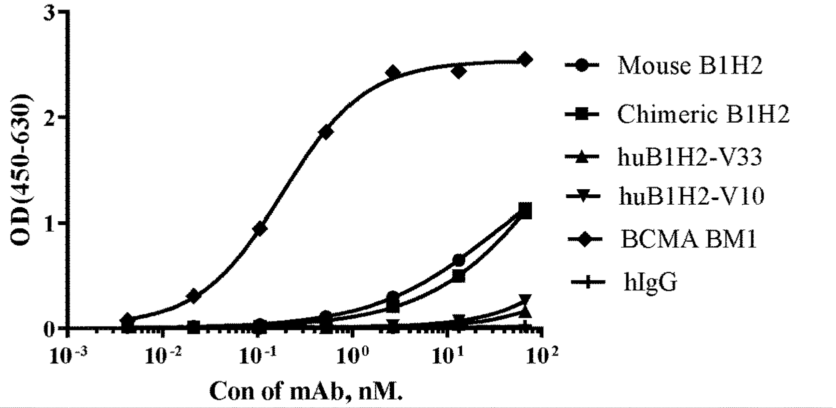
FIG. 6 shows the binding capacities of chimeric and humanized B1H2 antibodies to cynomolgus BCMA in an indirect ELISA.

It can be seen from FIG. 6 that the anti-BCMA humanized antibodies huB1H2-V10 and huB1H2-V33 did not bind Cynomolgus BCMA.

Figure 8:
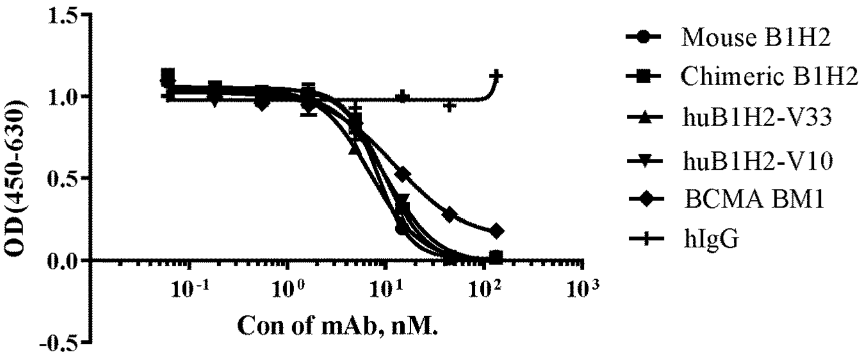
FIG. 8 shows the blocking abilities of chimeric and humanized B1H2 antibodies on human BCMA-BAFF binding in a competitive ELISA.
Figure 9:
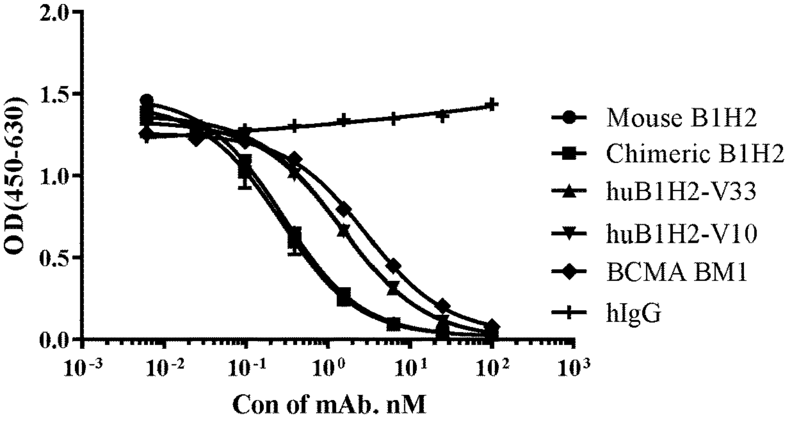
FIG. 9 shows the blocking abilities of chimeric and humanized B1H2 antibodies on benchmark-human BCMA binding in a competitive ELISA test.

FIG. 8 showed that mouse, chimeric and humanized B1H2 antibodies exhibited higher blocking abilities on BCMA-BAFF interaction than the control antibody.

Figure 10A:
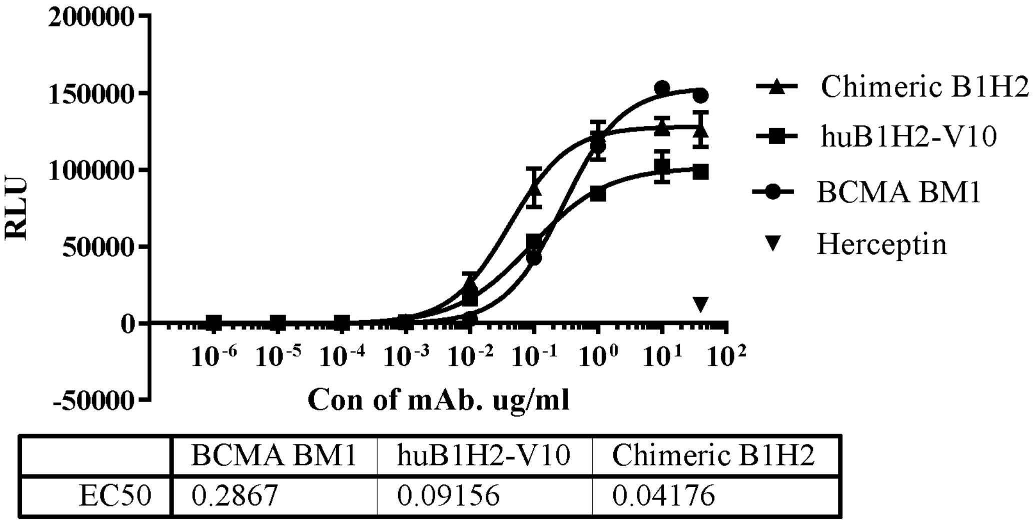
FIGS. 10A and 10B show the abilities of chimeric and humanized antibodies huB1H2-V10 (A) and huB1H2-V33 (B) to induce antibody-dependent cellular cytotoxicity (ADCC) against U266 cells in vitro.
Figure 10B:
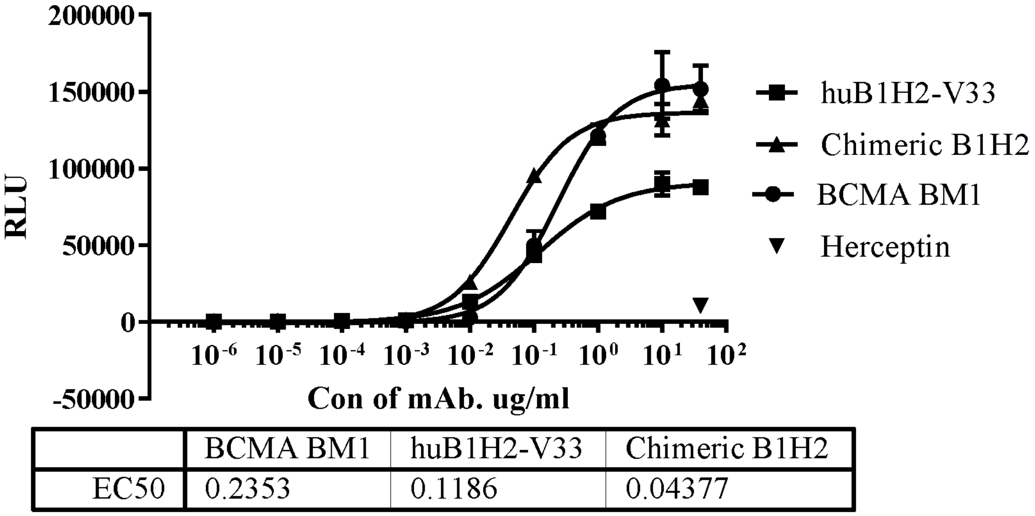

Further, as shown in FIGS. 10A-10B, chimeric and humanized B1H2 antibodies induced killing of U266 cells by Jurkat-NFAT-CD16a cells in a dose dependent manner. In specific, chimeric and humanized B1H2 antibodies induced higher ADCC at low doses than the BCMA BM1.

Figure 11:
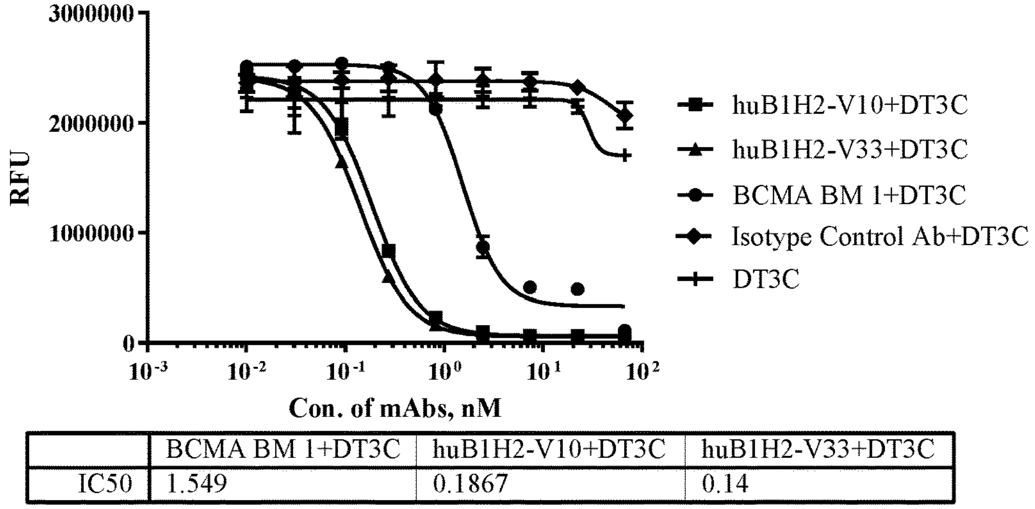
FIG. 11 shows the internalization-mediated cellular toxicities of humanized antibody-DT3C conjugates on U266 cells.

It can be seen from FIG. 11 and Table 6 that the anti-BCMA antibody-DT3C conjugates were internalized by U266 cells and caused cell death, while the recombinant protein DT3C alone or the isotype control-DT3C conjugate were hard to enter into the U266 cells and provided low cell killing activity. As compared to BCMA BM1-DT3C conjugate, the huB1H2-V10-DT3C conjugate and the huB1H2-V33-DT3C conjugate showed higher target cell killing activities, including lower $IC_{50}$s and higher maximum cell viability inhibition.

TABLE 6

| Cell killing activity of antibody-DT3C conjugates | | | | | |
|---|---|---|---|---|---|
| ADC | BM1-DT3C | huB1H2-V10-DT3C | huB1H2-V33-DT3C | Isotype Control-DT3C | DT3C |
| $IC_{50}$ (nM) | 1.55 | 0.19 | 0.14 | * | * |
| Max inhibition on cell viability (%) | 97.01 | 99.65 | 99.94 | 17.79 | 32.50 |

* No internalization

Figure 12A:
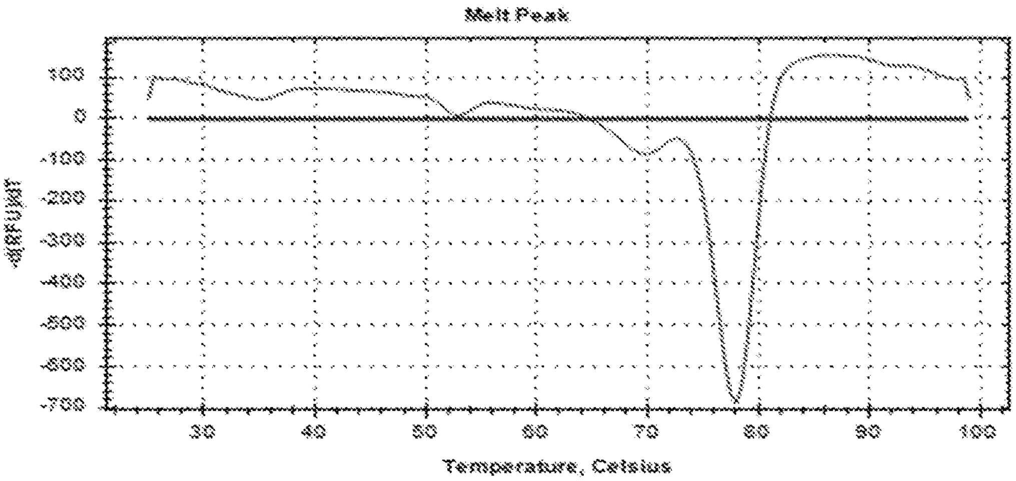
FIGS. 12A and 12B show the protein thermal shift assay results of humanized antibodies huB1H2-V10 (A) and huB1H2-V33 (B).
Figure 12B:
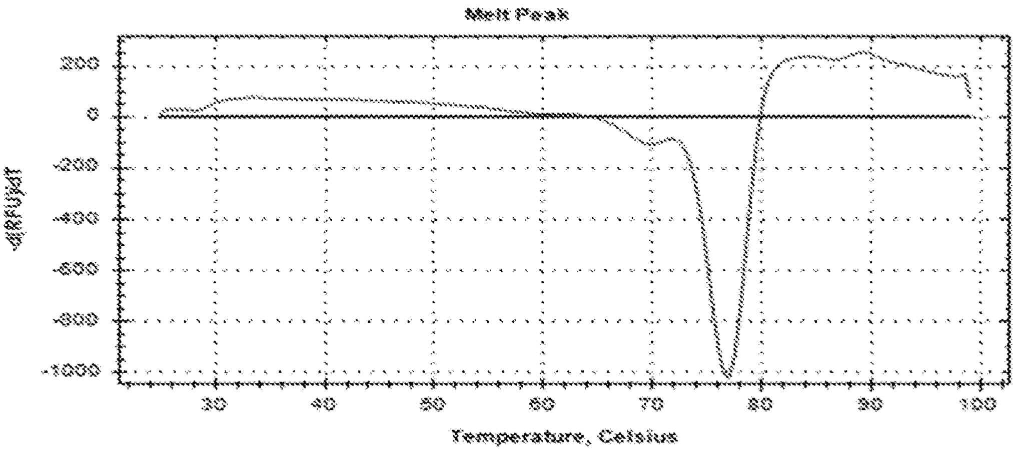

FIGS. 12A-12B showed that the anti-BCMA humanized antibodies huB1H2-V10 and huB1H2-V33 were probably stable in human body.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/<br>Sequence/SEQ ID NO. |
|---|
| VH CDR1 for mouse, chimeric and humanized B1H2<br>NYVMH (SEQ ID NO.: 1) |
| VH CDR2 for mouse, chimeric and humanized B1H2<br>FIIPFNDGTKYNEHFKG (SEQ ID NO.: 2) |
| VH CDR3 for mouse, chimeric and humanized B1H2<br>YDFEGYFDV (SEQ ID NO.: 3) |
| VL CDR1 formouse, chimeric and humanized B1H2<br>SASQDITNFLN (SEQ ID NO.: 4) |
| VL CDR2 for mouse, chimeric and humanized B1H2<br>STSRLHS (SEQ ID NO.: 5) |
| VL CDR3 for mouse, chimeric and humanized B1H2<br>QQYSNLPWT (SEQ ID NO.: 6) |
| VH for mouse and chimeric B1H2<br>EVQLQQSGPELVKPGASVKMSCKASGYTLTNYVMHWMKQKPGQGLEWIGFIIPFNDGTKYNE<br>HFKGKATLTSDKSSNTAYMVLSSLTSEDSAVYYCARYDFEGYFDVWGAGTTVTVSS<br>(SEQ ID NO.: 7) |
| VH for mouse B1H2<br>GAGGTCCAGTTGCAGCAGTCTGGACCTGAGCTGGTAAAGCCTGGGGCTTCAGTGAAGATGT<br>CCTGCAAGGCTTCTGGATACACATTAACTAACTATGTTATGCACTGGATGAAACAGAAGCC<br>TGGGCAGGGCCTTGAGTGGATTGGATTTATTATTCCTTTCAATGATGGTACTAAATACAATG<br>AGCACTTCAAAGGCAAGGCCACACTGACTTCAGACAAATCCTCCAACACAGCCTACATGGT<br>TCTCAGCAGCCTGACCTCTGAGGACTCTGCGGTCTATTACTGTGCAAGGTATGATTTCGAG<br>GGTTACTTCGATGTCTGGGGCGCAGGGACCACGGTCACCGTCTCCTCA<br>(SEQ ID NO.: 17) |
| VH for chimeric B1H2<br>GAGGTGCAGCTGCAGCAGAGCGGCCCTGAGCTGGTGAAGCCCGGCGCTTCCGTGAAGATG<br>AGCTGCAAGGCCAGCGGCTACACACTGACAAATTACGTGATGCACTGGATGAAGCAGAAG<br>CCCGGCCAGGGCCTGGAGTGGATCGGCTTCATCATCCCTTTTAACGACGGCACCAAGTACA<br>ACGAGCACTTTAAGGGCAAGGCCACACTGACATCCGACAAGAGCAGCAATACCGCCTACA<br>TGGTGCTGTCCAGCCTGACCAGCGAGGACTCCGCCGTGTACTACTGTGCCAGGTACGATTT<br>TGAGGGCTACTTCGACGTGTGGGGCGCCGGCACCACAGTGACCGTGAGCAGC<br>(SEQ ID NO.: 24) |
| VH for huB1H2-V1, huB1H2-V7, huB1H2-V13, and huB1H2-V19<br>EVQLVQSGAEVKKPGSSVKVSCKASGYTLTNYVMHWMRQAPGQGLEWIGFIIPFNDGTKYNE<br>HFKGRATLTSDKSTNTAYMELSSLRSEDTAVYYCARYDFEGYFDVWGAGTLVTVSS<br>(SEQ ID NO.: 8) |
| VH for huB1H2-V2, huB1H2-V8, huB1H2-V14, and huB1H2-V20<br>QVQLVQSGAEVKKPGASVKVSCKASGYTLTNYVMHWX1RQAPGQGLEWIGFIIPFNDGTKYN<br>EHFKGRVTITX2DX3SISTAYMQLSSLRSEDTAVYYCARYDFEGYFDVWGQGTLVTVSS<br>(SEQ ID NO.: 9) X1 = V, X2 = R, X3 = T |
| QVQLVQSGAEVKKPGASVKVSCKASGYTLTNYVMHWVRQAPGQGLEWIGFIIPFNDGTKYNE<br>HFKGRVTITRDTSISTAYMQLSSLRSEDTAVYYCARYDFEGYFDVWGQGTLVTVSS<br>(SEQ ID NO.: 26) |
| VH for huB1H2-V3, huB1H2-V9, huB1H2-V15, and huB1H2-V21<br>QVQLVQSGAEVKKPGASVKVSCKASGYTLTNYVMHWX1RQAPGQGLEWIGFIIPFNDGTKYN<br>EHFKGRVTITX2DX3SISTAYMQLSSLRSEDTAVYYCARYDFEGYFDVWGQGTLVTVSS<br>(SEQ ID NO.: 9) X1 = M, X2 = R, X3 = T |
| QVQLVQSGAEVKKPGASVKVSCKASGYTLTNYVMHWMRQAPGQGLEWIGFIIPFNDGTKYNE<br>HFKGRVTITRDTSISTAYMQLSSLRSEDTAVYYCARYDFEGYFDVWGQGTLVTVSS<br>(SEQ ID NO.: 27) |
| VH for huB1H2-V4, huB1H2-V10, huB1H2-V16, huB1H2-V22, and huB1H2-V33<br>QVQLVQSGAEVKKPGASVKVSCKASGYTLTNYVMHWX1RQAPGQGLEWIGFIIPFNDGTKYN<br>EHFKGRVTITX2DX3SISTAYMQLSSLRSEDTAVYYCARYDFEGYFDVWGQGTLVTVSS<br>(SEQ ID NO.: 9) X1 = V, X2 = S, X3 = T |
| QVQLVQSGAEVKKPGASVKVSCKASGYTLTNYVMHWVRQAPGQGLEWIGFIIPFNDGTKYNE<br>HFKGRVTITSDTSISTAYMQLSSLRSEDTAVYYCARYDFEGYFDVWGQGTLVTVSS<br>(SEQ ID NO.: 28) |
| CAGGTGCAGCTGGTGCAGAGCGGCGCCGAGGTGAAGAAGCCTGGCGCCTCCGTGAAGGTG<br>AGCTGCAAGGCCAGCGGCTACACACTGACAAATTACGTGATGCACTGGGTGAGACAGGCC |

-continued

| Description/ Sequence/SEQ ID NO. |
|---|
| CCTGGCCAGGGCCTGGAGTGGATCGGATTCATCATCCCCTTCAACGATGGCACCAAGTACA ATGAGCACTTCAAGGGCAGAGTGACCATCACCAGCGATACCTCCATCTCCACCGCCTACAT GCAGCTGTCCAGCCTGAGGTCCGAGGATACCGCCGTGTACTACTGCGCCAGGTACGACTTC GAGGGCTACTTCGACGTGTGGGGCCAGGGCACCCTGGTGACCGTGTCCAGC (SEQ ID NO. 18) |
| VH for huB1H2-V5, huB1H2-Vl 1, huB1H2-V17, and huB1H2-V23 QVQLVQSGAEVKKPGASVKVSCKASGYTLTNYVMHWX1RQAPGQGLEWIGFIIPFNDGTKYN EHFKGRVTITX2DX3SISTAYMQLSSLRSEDTAVYYCARYDFEGYFDVWGQGTLVTVSS (SEQ ID NO.: 9) X1 = V, X2 = R, X3 = K |
| QVQLVQSGAEVKKPGASVKVSCKASGYTLTNYVMHWVRQAPGQGLEWIGFIIPFNDGTKYNE HFKGRVTITRDKSISTAYMQLSSLRSEDTAVYYCARYDFEGYFDVWGQGTLVTVSS (SEQ ID NO.: 29) |
| VH for huB1H2-V6, huB1H2-V12, huB1H2-V18, and huB1H2-V24 QVQLVQSGAEVKKPGASVKVSCKASGYTLTNYVMHWX1RQAPGQGLEWIGFIIPFNDGTKYN EHFKGRVTITX2DX3SISTAYMQLSSLRSEDTAVYYCARYDFEGYFDVWGQGTLVTVSS (SEQ ID NO.: 9) X1 = V, X2 = S, X3 = K |
| QVQLVQSGAEVKKPGASVKVSCKASGYTLTNYVMHWVRQAPGQGLEWIGFIIPFNDGTKYNE HFKGRVTITSDKSISTAYMQLSSLRSEDTAVYYCARYDFEGYFDVWGQGTLVTVSS (SEQ ID NO.: 30) |
| VL for mouse and chimeric B1H2 DIQMTQTTSSLSASLGDRVTISCSASQDITNFLNWYQQKPDGTVKLLIYSTSRLHSGVPSRFSGS GSGTDYSLTISNLEPEDIATYYCQQYSNLPWTFGGGTNLEIK (SEQ ID NO.: 10) |
| VL for mouse B1H2 GATATCCAGATGACACAGACTACATCCTCCCTGTCTGCCTCTCTGGGAGACAGAGTCACCA TCAGTTGCAGTGCAAGTCAGGACATTACCAATTTTTTAAACTGGTATCAGCAGAAACCAGA TGGAACTGTTAAACTCCTGATCTATTCCACATCAAGATTACACTCAGGAGTCCCATCAAGG TTCAGTGGCAGTGGGTCTGGGACAGATTATTCTCTCACCATCAGCAACCTGGAACCTGAAG ATATTGCCACTTACTATTGTCAGCAGTATAGTAACCTTCCGTGGACGTTCGGTGGCGGCACC AACCTGGAAATCAAA (SEQ ID NO.: 19) |
| VL for chimeric B1H2 GACATCCAGATGACCCAGACAACAAGCAGCCTGAGCGCCTCCCTGGGCGACAGGGTGACA ATCTCCTGCAGCGCCAGCCAGGACATCACAAACTTCCTGAACTGGTATCAACAGAAGCCCG ACGGCACAGTGAAGCTGCTGATCTACTCCACATCCAGACTGCACTCCGGCGTGCCCTCCAG GTTCTCCGGCTCCGGATCCGGCACAGATTACTCCCTGACCATCAGCAACCTGGAGCCTGAG GACATCGCCACCTACTACTGCCAGCAGTACAGCAATCTGCCTTGGACCTTTGGCGGCGGCA CCAATCTGGAGATCAAG (SEQ ID NO.: 25) |
| VL for huB1H2-V1 - huB1H2-V6 DIQMTQSPSSLSASVGDRVTITCSASQDITNFLNWYQQKPGKX1X2KLLIYSTSRLHSGVPSRFSG SGSGTDX3TX4TISSLQPEDIATYYCQQYSNLPWTFGQGTKVEIK (SEQ ID NO.: 11) X1 = T, X2 = V, X3 = Y, X4 = F |
| DIQMTQSPSSLSASVGDRVTITCSASQDITNFLNWYQQKPGKTVKLLIYSTSRLHSGVPSRFSGS GSGTDYTFTISSLQPEDIATYYCQQYSNLPWTFGQGTKVEIK (SEQ ID NO.: 31) |
| VL for huB1H2-V7 - huB1H2-V12 DIQMTQSPSSLSASVGDRVTITCSASQDITNFLNWYQQKPGKX1X2KLLIYSTSRLHSGVPSRFSG SGSGTDX3TX4TISSLQPEDIATYYCQQYSNLPWTFGQGTKVEIK (SEQ ID NO.: 11) X1 = A, X2 = P, X3 = F, X4 = L |
| DIQMTQSPSSLSASVGDRVTITCSASQDITNFLNWYQQKPGKAPKLLIYSTSRLHSGVPSRFSGS GSGTDFTLTISSLQPEDIATYYCQQYSNLPWTFGQGTKVEIK (SEQ ID NO.: 32) |
| VL for huB1H2-V13 - huB1H2-V18 DIQMTQSPSSLSASVGDRVTITCSASQDITNFLNWYQQKPGKX1X2KLLIYSTSRLHSGVPSRFSG SGSGTDX3TX4TISSLQPEDIATYYCQQYSNLPWTFGQGTKVEIK (SEQ ID NO.: 11) X1 = A, X2 = V, X3 = F, X4 = L |
| DIQMTQSPSSLSASVGDRVTITCSASQDITNFLNWYQQKPGKAVKLLIYSTSRLHSGVPSRFSGS GSGTDFTLTISSLQPEDIATYYCQQYSNLPWTFGQGTKVEIK (SEQ ID NO.: 33) |
| VL for huB1H2-V19 - huB1H2-V24 DIQMTQSPSSLSASVGDRVTITCSASQDITNFLNWYQQKPGKX1X2KLLIYSTSRLHSGVPSRFSG SGSGTDX3TX4TISSLQPEDIATYYCQQYSNLPWTFGQGTKVEIK (SEQ ID NO.: 11) X1 = A, X2 = P, X3 = Y, X4 = L |

-continued

| Description/ Sequence/SEQ ID NO. |
|---|
| DIQMTQSPSSLSASVGDRVTITCSASQDITNFLNWYQQKPGKAPKLLIYSTSRLHSGVPSRFSGS GSGTDYTLTISSLQPEDIATYYCQQYSNLPWTFGQGTKVEIK (SEQ ID NO.: 34) |
| VL for huB1H2-V33 DIQMTQSPSSLSASVGDRVTITCSASQDITNFLNWYQQKPGKX1X2KLLIYSTSRLHSGVPSRFSG SGSGTDX3TX4TISSLQPEDIATYYCQQYSNLPWTFGQGTKVEIK (SEQ ID NO.: 11) X1 = A, X2 = P, X3 = F, X4 = F |
| DIQMTQSPSSLSASVGDRVTITCSASQDITNFLNWYQQKPGKAPKLLIYSTSRLHSGVPSRFSGS GSGTDFTFTISSLQPEDIATYYCQQYSNLPWTFGQGTKVEIK (SEQ ID NO.: 35) |
| GACATCCAGATGACACAGAGCCCCTCCAGCCTGAGCGCCAGCGTGGGAGATAGGGTGACC ATCACCTGTAGCGCCTCCCAGGATATCACCAACTTCCTGAATTGGTATCAACAGAAGCCCG GCAAGGCCCCCAAGCTGCTGATCTACTCCACCTCCAGACTGCACAGCGGCGTGCCTTCCAG GTTCAGCGGCTCCGGCTCCGGCACAGACTTCACCTTCACCATCTCCAGCCTGCAGCCTGAG GATATCGCCACCTACTACTGCCAGCAGTACAGCAATCTGCCCTGGACCTTCGGCCAGGGCA CCAAGGTGGAGATCAAG (SEQ ID NO.: 20) |
| Heavy chain constant region for chimeric and humanized antibodies ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALHN HYTQKSLSLSPGK (SEQ ID NO.: 12) |
| GCTAGCACCAAGGGCCCATCGGTCTTCCCCCTGGCACCCTCCTCCAAGAGCACCTCTGGGG GCACAGCGGCCCTGGGCTGCCTGGTCAAGGACTACTTCCCCGAACCGGTGACGGTGTCGTG GAACTCAGGCGCCCTGACCAGCGGCGTGCACACCTTCCCGGCTGTCCTACAGTCCTCAGGA CTCTACTCCCTCAGCAGCGTGGTGACCGTGCCCTCCAGCAGCTTGGGCACCCAGACCTACA TCTGCAACGTGAATCACAAGCCCAGCAACACCAAGGTGGACAAGAAAGTTGAGCCCAAAT CTTGTGACAAAACTCACACATGCCCACCGTGCCCAGCACCTGAACTCCTGGGGGGACCGTC AGTCTTCCTCTTCCCCCCAAAACCCAAGGACACCCTCATGATCTCCCGGACCCCTGAGGTC ACATGCGTGGTGGTGGACGTGAGCCACGAAGACCCTGAGGTCAAGTTCAACTGGTACGTG GACGGCGTGGAGGTGCATAATGCCAAGACAAAGCCGCGGGAGGAGCAGTACAACAGCAC GTACCGTGTGGTCAGCGTCCTCACCGTCCTGCACCAGGACTGGCTGAATGGCAAGGAGTAC AAGTGCAAGGTCTCCAACAAAGCCCTCCCAGCCCCCATCGAGAAAACCATCTCCAAAGCC AAAGGGCAGCCCCGAGAACCACAGGTGTACACCCTGCCCCCATCCCGGGAGGAGATGACC AAGAACCAGGTCAGCCTGACCTGCCTGGTCAAAGGCTTCTATCCCAGCGACATCGCCGTGG AGTGGGAGAGCAATGGGCAGCCGGAGAACAACTACAAGACCACGCCTCCCGTGCTGGACT CCGACGGCTCCTTCTTCCTCTACAGCAAGCTCACCGTGGACAAGAGCAGGTGGCAGCAGGG GAACGTCTTCTCATGCTCCGTGATGCATGAGGCTCTGCACAACCACTACACGCAGAAGAGC CTCTCCCTGTCTCCGGGTAAATGA (SEQ ID NO.: 21) |
| Light chain constant region for chimeric and humanized antibodies RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC (SEQ ID NO.: 13) |
| CGTACGGTGGCGGCGCCATCTGTCTTCATCTTCCCGCCATCTGATGAGCAGTTGAAATCTGG AACTGCCTCTGTTGTGTGCCTGCTGAATAACTTCTATCCCAGAGAGGCCAAAGTACAGTGG AAGGTGGATAACGCCCTCCAATCGGGTAACTCCCAGGAGAGTGTCACAGAGCAGGACAGC AAGGACAGCACCTACAGCCTCAGCAGCACCCTGACGCTGAGCAAAGCAGACTACGAGAAA CACAAAGTCTACGCCTGCGAAGTCACCCATCAGGGCCTGAGCTCGCCCGTCACAAAGAGCT TCAACAGGGGAGAGTGTTGA (SEQ ID NO.: 22) |
| Heavy chain of BCMA BM1 QVQLVQSGAEVKKPGSSVKVSCKASGGTFSNYWMHWVRQAPGQGLEWMGATYRGHSDTYY NQKFKGRVTITADKSTSTAYMELSSLRSEDTAVYYCARGAIYDGYDVLDNWGQGTLVTVSSA STKGPSVFPLAPSSKSTSGGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVMHEALHNHY TQKSLSLSPGK (SEQ ID NO.: 14) |
| Light chain of BCMA BM1 DIQMTQSPSSLSASVGDRVTITCSASQDISNYLNWYQQKPGKAPKLLIYYTSNLHSGVPSRFSGS GSGTDFTLTISSLQPEDFATYYCQQYRKLPWTFGQGTKLEIKRTVAAPSVFIFPPSDEQLKSGTA SVVCLLNNFYPREAKVQWKVDNALQSGNSQESVTEQDSKDSTYSLSSTLTLSKADYEKHKVY ACEVTHQGLSSPVTKSFNRGEC (SEQ ID NO.: 15) |

-continued

| Description/ Sequence/SEQ ID NO. |
|---|
| Full length human BCMA<br>MLQMAGQCSQNEYFDSLLHACIPCQLRCSSNTPPLTCQRYCNASVTNSVKGTNAILWTCLGLS<br>LIISLAVFVLMFLLRKINSEPLKDEFKNTGSGLLGMANIDLEKSRTGDEIILPRGLEYTVEECTCE<br>DCIKSKPKVDSDHCFPLPAMEEGATILVTTKTNDYCKSLPAALSATEIEKSISAR<br>(SEQ ID NO.: 16) |
| Recombinant protein DT3C<br>MGADDVVDSSKSFVMENFSSYHGTKPGYVDSIQKGIQKPKSGTQGNYDDDWKGFYSTDNKY<br>DAAGYSVDNENPLSGKAGGVVKVTYPGLTKVLALKVDNAETIKKELGLSLTEPLMEQVGTEEF<br>IKRFGDGASRVVLSLPFAEGSSSVEYINNWEQAKALSVELEINFETRGKRGQDAMYEYMAQAC<br>AGNRVRRSVGSSLSCINLDWDVIRDKTKTKIESLKEHGPIKNKMSESPNKTVSEEKAKQYLEEF<br>HQTALEHPELSELKTVTGTNPVFAGANYAAWAVNVAQVIDSETADNLEKTTAALSILPGIGSV<br>MGIADGAVHHNTEEIVAQSIALSSLMVAQAIPLVGELVDIGFAAYNFVESIINLFQVVHNSYNRP<br>AYSPGHKHIDEILAALPKTDTYKLILNGKTLKGETTTEAVDAATAEKVFKQYANDNGVDGEWT<br>YDDATKTFTVTEKPEVIDASELTPAVTTYKLVINGKTLKGETTTEAVDAATAEKVFKQYANDN<br>GVDGEWTYDDATKTFTVTEKPEVIDASELTPAVTTYKLVINGKTLKGETTTKAVDAETAEKAF<br>KQYANDNGVDGVWTYDDATKTFTVTE (SEQ ID NO: 23) |

We claim:

1. An isolated monoclonal antibody, or an antigen-binding portion thereof, specifically binding to B cell maturation antigen (BCMA), comprising i) a heavy chain variable region comprising a VH CDR1 region, a VH CDR2 region and a VH CDR3 region, wherein the VH CDR1 region, the VH CDR2 region and the VH CDR3 region comprise amino acid sequences of SEQ ID NOs: 1, 2 and 3, respectively; and ii) a light chain variable region comprising a VL CDR1 region, a VL CDR2 region and a VL CDR3 region, wherein the VL CDR1 region, the VL CDR2 region and the VL CDR3 region comprise amino acid sequences of SEQ ID NOs: 4, 5 and 6, respectively.

2. The isolated monoclonal antibody, or the antigen-binding portion thereof, of claim 1, wherein the heavy chain variable region comprises an amino acid sequence having at least 95%, sequence identity to SEQ ID NOs: 7, 8, or 9, wherein 37$^{th}$, 72$^{nd}$ and 74$^{th}$ amino acid residues in SEQ ID NO: 9 are V, R and T, respectively; M, R and T, respectively; V, S and T, respectively; V, R and K, respectively; or V, S and K, respectively.

3. The isolated monoclonal antibody, or the antigen-binding portion thereof, of claim 1, wherein the light chain variable region comprises an amino acid sequence having at least 95% sequence identity to SEQ ID NOs: 10 or 11, wherein 43$^{rd}$, 44$^{th}$, 71$^{st}$ and 73$^{rd}$ amino acid residues in SEQ ID NO: 11 are T, V, Y and F, respectively; A, P, F and L, respectively; A, P, Y and L, respectively; A, V, F and L, respectively; or A, P, F and F, respectively.

4. The isolated monoclonal antibody, or the antigen-binding portion thereof, of claim 2, wherein the heavy chain variable region and the light chain variable region comprise the amino acid sequences of (1) SEQ ID NOs: 7 and 10, respectively;

(2) SEQ ID NOs: 8 and 11, respectively, wherein 43$^{rd}$, 44$^{th}$, 71$^{st}$ and 73$^{rd}$ amino acid residues in SEQ ID NO: 11 are T, V, Y and F, respectively; A, P, F and L, respectively; A, P, Y and L, respectively; or A, V, F and L, respectively;

(3) SEQ ID NOs: 9 and 11, respectively, wherein 37$^{th}$, 72$^{nd}$ and 74$^{th}$ amino acid residues in SEQ ID NO: 9 are V, R and T, respectively; M, R and T, respectively; V, S and T, respectively; V, R and K, respectively; or V, S and K, respectively, wherein 43$^{rd}$, 44$^{th}$, 71$^{st}$ and 73$^{rd}$ amino acid residues in SEQ ID NO: 11 are T, V, Y and F, respectively;

(4) SEQ ID NOs: 9 and 11, respectively, wherein 37$^{th}$, 72$^{nd}$ and 74$^{th}$ amino acid residues in SEQ ID NO: 9 are V, R and T, respectively; M, R and T, respectively; V, S and T, respectively; V, R and K, respectively; or V, S and K, respectively, wherein 43$^{rd}$, 44$^{th}$, 71$^{st}$ and 73$^{rd}$ amino acid residues in SEQ ID NO: 11 are A, P, F and L, respectively;

(5) SEQ ID NOs: 9 and 11, respectively, wherein 37$^{th}$, 72$^{nd}$ and 74$^{th}$ amino acid residues in SEQ ID NO: 9 are V, R and T, respectively; M, R and T, respectively; V, S and T, respectively; V, R and K, respectively; or V, S and K, respectively, wherein 43$^{rd}$, 44$^{th}$, 71$^{st}$ and 73$^{rd}$ amino acid residues in SEQ ID NO: 11 are A, P, Y and L, respectively;

(6) SEQ ID NOs: 9 and 11, respectively, wherein 37$^{th}$, 72$^{nd}$ and 74$^{th}$ amino acid residues in SEQ ID NO: 9 are V, R and T, respectively; M, R and T, respectively; V, S and T, respectively; V, R and K, respectively; or V, S and K, respectively, wherein 43$^{rd}$, 44$^{th}$, 71$^{st}$ and 73$^{rd}$ amino acid residues in SEQ ID NO: 11 are A, V, F and L, respectively; or (7) SEQ ID NOs: 9 and 11, respectively, wherein 37$^{th}$, 72$^{nd}$ and 74$^{th}$ amino acid residues in SEQ ID NO: 9 are V, S and T, respectively, wherein 43$^{rd}$, 44$^{th}$, 71$^{st}$ and 73$^{rd}$ amino acid residues in SEQ ID NO: 11 are A, P, F and F, respectively.

5. The isolated monoclonal antibody, or the antigen-binding portion thereof, of claim 4, comprising a heavy chain constant region comprising the amino acid sequence of SEQ ID NO: 12, linked to the heavy chain variable region, and a light chain constant region comprising the amino acid sequence of SEQ ID NO: 13, linked to the light chain variable region.

6. The isolated monoclonal antibody, or the antigen-binding portion thereof, of claim 1, comprising an Fc region that binds to FcγRIIIa, which (a) binds human BCMA; (b) blocks human BCMA-human BAFF binding; and (c) induces antibody dependent cell mediated cytotoxicity (ADCC) against BCMA expressing cells.

7. The isolated monoclonal antibody, or the antigen-binding portion thereof, of claim 1, which is a mouse, chimeric or humanized antibody or antigen-binding portion thereof.

8. The isolated monoclonal antibody, or the antigen-binding portion thereof, of claim 1, which is an IgG1, IgG2 or IgG4 isotype.

9. A pharmaceutical composition comprising i) the isolated monoclonal antibody, or the antigen-binding portion thereof, of claim 1, and ii) a pharmaceutically acceptable carrier.

10. An immunoconjugate comprising the isolated monoclonal antibody, or the antigen-binding portion thereof, of claim 1, conjugated to an additional therapeutic agent.

11. The immunoconjugate of claim 10, wherein the isolated monoclonal antibody or the antigen-binding portion thereof is linked to a cytotoxin.

12. The immunoconjugate of claim 11, wherein the cytotoxin is a recombinant protein comprising the amino acid sequence of SEQ ID NO: 23.

13. A pharmaceutical composition comprising the immunoconjugate of claim 11, and a pharmaceutically acceptable carrier.

14. A method for treating a tumor associated with increased BCMA expression in a subject, comprising administering to the subject a therapeutically effective amount of the pharmaceutical composition of claim 9.

15. The method of claim 14, wherein the tumor is leukemia, lymphomas or multiple myeloma.

16. A method for treating a tumor associated with increased BCMA expression in a subject, comprising administering to the subject a therapeutically effective amount of the pharmaceutical composition of claim 13.

17. The method of claim 16, wherein the tumor is leukemia, lymphomas or multiple myeloma.

* * * * *

SEQUENCE LISTING

```
<160> NUMBER OF SEQ ID NOS: 35

<210> SEQ ID NO 1
<211> LENGTH: 5
<212> TYPE: PRT
<213> ORGANISM: Artificial Sequence
<220> FEATURE:
<223> OTHER INFORMATION: VH CDR1 for mouse, chimeric and humanized B1H2

<400> SEQUENCE: 1

Asn Tyr Val Met His
1               5


<210> SEQ ID NO 2
<211> LENGTH: 17
<212> TYPE: PRT
<213> ORGANISM: Artificial Sequence
<220> FEATURE:
<223> OTHER INFORMATION: VH CDR2 for mouse, chimeric and humanized B1H2

<400> SEQUENCE: 2

Phe Ile Ile Pro Phe Asn Asp Gly Thr Lys Tyr Asn Glu His Phe Lys
1               5                   10                  15

Gly


<210> SEQ ID NO 3
<211> LENGTH: 9
<212> TYPE: PRT
<213> ORGANISM: Artificial Sequence
<220> FEATURE:
<223> OTHER INFORMATION: VH CDR3 for mouse, chimeric and humanized B1H2

<400> SEQUENCE: 3

Tyr Asp Phe Glu Gly Tyr Phe Asp Val
1               5


<210> SEQ ID NO 4
<211> LENGTH: 11
<212> TYPE: PRT
<213> ORGANISM: Artificial Sequence
<220> FEATURE:
<223> OTHER INFORMATION: VL CDR1 for mouse, chimeric and humanized B1H2

<400> SEQUENCE: 4
```

Ser Ala Ser Gln Asp Ile Thr Asn Phe Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR2 for mouse, chimeric and humanized B1H2

<400> SEQUENCE: 5

Ser Thr Ser Arg Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR3 for mouse, chimeric and humanized B1H2

<400> SEQUENCE: 6

Gln Gln Tyr Ser Asn Leu Pro Trp Thr
1               5

<210> SEQ ID NO 7
<211> LENGTH: 118
<212> TYPE: PRT
<213> ORGANISM: Artificial Sequence
<220> FEATURE:
<223> OTHER INFORMATION: VH for mouse and chimeric B1H2

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Leu Thr Asn Tyr
            20                  25                  30

Val Met His Trp Met Lys Gln Lys Pro Gly Gln Gly Leu Glu Trp Ile
        35                  40                  45

Gly Phe Ile Ile Pro Phe Asn Asp Gly Thr Lys Tyr Asn Glu His Phe
    50                  55                  60

Lys Gly Lys Ala Thr Leu Thr Ser Asp Lys Ser Ser Asn Thr Ala Tyr
65                  70                  75                  80

Met Val Leu Ser Ser Leu Thr Ser Glu Asp Ser Ala Val Tyr Tyr Cys
                85                  90                  95

Ala Arg Tyr Asp Phe Glu Gly Tyr Phe Asp Val Trp Gly Ala Gly Thr
            100                 105                 110

Thr Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: VH for huB1H2-V1, huB1H2-V7, huB1H2-V13, and
      huB1H2-V19

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Asn Tyr
            20                  25                  30

Val Met His Trp Met Arg Gln Ala Pro Gly Gln Gly Leu Glu Trp Ile
35 40 45

Gly Phe Ile Ile Pro Phe Asn Asp Gly Thr Lys Tyr Asn Glu His Phe
50 55 60

Lys Gly Arg Ala Thr Leu Thr Ser Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Tyr Asp Phe Glu Gly Tyr Phe Asp Val Trp Gly Ala Gly Thr
100 105 110

Leu Val Thr Val Ser Ser
115

<210> SEQ ID NO 9
<211> LENGTH: 118
<212> TYPE: PRT
<213> ORGANISM: Artificial Sequence
<220> FEATURE:
<223> OTHER INFORMATION: VH for huB1H2-V2 to huB1H2-V6, huB1H2-V8 to huB1H2-V12, huB1H2-V14 to huB1H2-V18, huB1H2-V20 to huB1H2-V24, and huB1H2-V33
<220> FEATURE:
<221> NAME/KEY: misc_feature
<222> LOCATION: (37)..(37)
<223> OTHER INFORMATION: Xaa can be Val or Met
<220> FEATURE:
<221> NAME/KEY: misc_feature
<222> LOCATION: (72)..(72)
<223> OTHER INFORMATION: Xaa can be Arg or Ser
<220> FEATURE:
<221> NAME/KEY: misc_feature
<222> LOCATION: (74)..(74)
<223> OTHER INFORMATION: Xaa can be Thr or Lys

<400> SEQUENCE: 9

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Thr Asn Tyr
20 25 30

Val Met His Trp Xaa Arg Gln Ala Pro Gly Gln Gly Leu Glu Trp Ile
35 40 45

Gly Phe Ile Ile Pro Phe Asn Asp Gly Thr Lys Tyr Asn Glu His Phe
50 55 60

Lys Gly Arg Val Thr Ile Thr Xaa Asp Xaa Ser Ile Ser Thr Ala Tyr
65 70 75 80

Met Gln Leu Ser Ser Leu Arg Ser Glu Asp Thr Ala Val Tyr Tyr Cys
85 90 95

Ala Arg Tyr Asp Phe Glu Gly Tyr Phe Asp Val Trp Gly Gln Gly Thr
100 105 110

Leu Val Thr Val Ser Ser
115

<210> SEQ ID NO 10
<211> LENGTH: 107
<212> TYPE: PRT
<213> ORGANISM: Artificial Sequence
<220> FEATURE:
<223> OTHER INFORMATION: VL for mouse and chimeric B1H2

<400> SEQUENCE: 10

Asp Ile Gln Met Thr Gln Thr Thr Ser Ser Leu Ser Ala Ser Leu Gly
1 5 10 15

```
Asp Arg Val Thr Ile Ser Cys Ser Ala Ser Gln Asp Ile Thr Asn Phe
            20                  25                  30

Leu Asn Trp Tyr Gln Gln Lys Pro Asp Gly Thr Val Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asn Leu Pro Trp
                85                  90                  95

Thr Phe Gly Gly Gly Thr Asn Leu Glu Ile Lys
            100                 105


<210> SEQ ID NO 11
<211> LENGTH: 107
<212> TYPE: PRT
<213> ORGANISM: Artificial Sequence
<220> FEATURE:
<223> OTHER INFORMATION: VL for huB1H2-V1 to huB1H2-V24 and huB1H2-V33
<220> FEATURE:
<221> NAME/KEY: misc_feature
<222> LOCATION: (43)..(43)
<223> OTHER INFORMATION: Xaa can be Thr or Ala
<220> FEATURE:
<221> NAME/KEY: misc_feature
<222> LOCATION: (44)..(44)
<223> OTHER INFORMATION: Xaa can be Val or Pro
<220> FEATURE:
<221> NAME/KEY: misc_feature
<222> LOCATION: (71)..(71)
<223> OTHER INFORMATION: Xaa can be Tyr or Phe
<220> FEATURE:
<221> NAME/KEY: misc_feature
<222> LOCATION: (73)..(73)
<223> OTHER INFORMATION: Xaa can be Phe or Leu

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Thr Asn Phe
            20                  25                  30

Leu Asn Trp Tyr Gln Gln Lys Pro Gly Lys Xaa Xaa Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Xaa Thr Xaa Thr Ile Ser Ser Leu Gln Pro
65                  70                  75                  80

Glu Asp Ile Ala Thr Tyr Tyr Cys Gln Gln Tyr Ser Asn Leu Pro Trp
                85                  90                  95

Thr Phe Gly Gln Gly Thr Lys Val Glu Ile Lys
            100                 105


<210> SEQ ID NO 12
<211> LENGTH: 330
<212> TYPE: PRT
<213> ORGANISM: Artificial Sequence
<220> FEATURE:
<223> OTHER INFORMATION: Heavy chain constant region for chimeric and
      humanized antibodies

<400> SEQUENCE: 12

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 13
<211> LENGTH: 107
<212> TYPE: PRT
<213> ORGANISM: Artificial Sequence
<220> FEATURE:
<223> OTHER INFORMATION: Light chain constant region for chimeric and
      humanized antibodies

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 14
<211> LENGTH: 451
<212> TYPE: PRT
<213> ORGANISM: Artificial Sequence
<220> FEATURE:
<223> OTHER INFORMATION: Heavy chain of BCMA BM1

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Glu Asn Trp Tyr Val Asp Gly Val Glu Val
        275                 280                 285

His Asn Ala Lys Thr Lys Pro Arg Glu Glu Gln Tyr Asn Ser Thr Tyr
```

290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 15
<211> LENGTH: 214
<212> TYPE: PRT
<213> ORGANISM: Artificial Sequence
<220> FEATURE:
<223> OTHER INFORMATION: Light chain of BCMA BM1

<400> SEQUENCE: 15

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Asn Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Arg Lys Leu Pro Trp
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser

```
        195                 200                 205

Phe Asn Arg Gly Glu Cys
    210


<210> SEQ ID NO 16
<211> LENGTH: 184
<212> TYPE: PRT
<213> ORGANISM: Homo sapiens

<400> SEQUENCE: 16

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 17
<211> LENGTH: 354
<212> TYPE: DNA
<213> ORGANISM: Artificial Sequence
<220> FEATURE:
<223> OTHER INFORMATION: VH for mouse B1H2

<400> SEQUENCE: 17

gaggtccagt tgcagcagtc tggacctgag ctggtaaagc ctggggcttc agtgaagatg      60

tcctgcaagg cttctggata cacattaact aactatgtta tgcactggat gaaacagaag     120

cctgggcagg gccttgagtg gattggattt attattcctt tcaatgatgg tactaaatac     180

aatgagcact tcaaaggcaa ggccacactg acttcagaca aatcctccaa cacagcctac     240

atggttctca gcagcctgac ctctgaggac tctgcggtct attactgtgc aaggtatgat     300

ttcgagggtt acttcgatgt ctggggcgca gggaccacgg tcaccgtctc ctca           354


<210> SEQ ID NO 18
<211> LENGTH: 354
<212> TYPE: DNA
<213> ORGANISM: Artificial Sequence
<220> FEATURE:
<223> OTHER INFORMATION: VH for huB1H2-V4, huB1H2-V10, huB1H2-V16,
      huB1H2-V22, and huB1H2-V33
```

<400> SEQUENCE: 18
caggtgcagc tggtgcagag cggcgccgag gtgaagaagc ctggcgcctc cgtgaaggtg 60
agctgcaagg ccagcggcta cacactgaca aattacgtga tgcactgggt gagacaggcc 120
cctggccagg gcctggagtg gatcggattc atcatcccct tcaacgatgg caccaagtac 180
aatgagcact tcaagggcag agtgaccatc accagcgata cctccatctc caccgcctac 240
atgcagctgt ccagcctgag gtccgaggat accgccgtgt actactgcgc caggtacgac 300
ttcgagggct acttcgacgt gtggggccag ggcaccctgg tgaccgtgtc cagc 354

<210> SEQ ID NO 19
<211> LENGTH: 321
<212> TYPE: DNA
<213> ORGANISM: Artificial Sequence
<220> FEATURE:
<223> OTHER INFORMATION: VL for mouse B1H2

<400> SEQUENCE: 19
gatatccaga tgacacagac tacatcctcc ctgtctgcct ctctgggaga cagagtcacc 60
atcagttgca gtgcaagtca ggacattacc aatttttaa actggtatca gcagaaacca 120
gatggaactg ttaaactcct gatctattcc acatcaagat tacactcagg agtcccatca 180
aggttcagtg gcagtgggtc tgggacagat tattctctca ccatcagcaa cctggaacct 240
gaagatattg ccacttacta ttgtcagcag tatagtaacc ttccgtggac gttcggtggc 300
ggcaccaacc tggaaatcaa a 321

<210> SEQ ID NO 20
<211> LENGTH: 321
<212> TYPE: DNA
<213> ORGANISM: Artificial Sequence
<220> FEATURE:
<223> OTHER INFORMATION: VL for huB1H2-V33

<400> SEQUENCE: 20
gacatccaga tgacacagag cccctccagc ctgagcgcca gcgtgggaga tagggtgacc 60
atcacctgta gcgcctccca ggatatcacc aacttcctga attggtatca acagaagccc 120
ggcaaggccc ccaagctgct gatctactcc acctccagac tgcacagcgg cgtgccttcc 180
aggttcagcg gctccggctc cggcacagac ttcaccttca ccatctccag cctgcagcct 240
gaggatatcg ccacctacta ctgccagcag tacagcaatc tgccctggac cttcggccag 300
ggcaccaagg tggagatcaa g 321

<210> SEQ ID NO 21
<211> LENGTH: 993
<212> TYPE: DNA
<213> ORGANISM: Artificial Sequence
<220> FEATURE:
<223> OTHER INFORMATION: Heavy chain constant region for chimeric and
humanized antibodies

<400> SEQUENCE: 21
gctagcacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300

```
aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa tga                                 993
```

<210> SEQ ID NO 22
<211> LENGTH: 324
<212> TYPE: DNA
<213> ORGANISM: Artificial Sequence
<220> FEATURE:
<223> OTHER INFORMATION: Light chain constant region for chimeric and humanized antibodies

<400> SEQUENCE: 22

```
cgtacggtgg cggcgccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg ttga                                           324
```

<210> SEQ ID NO 23
<211> LENGTH: 594
<212> TYPE: PRT
<213> ORGANISM: Artificial Sequence
<220> FEATURE:
<223> OTHER INFORMATION: Recombinant protein DT3C

<400> SEQUENCE: 23

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110
```

-continued

```
Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys His Ile Asp Glu Ile Leu Ala Ala Leu Pro Lys Thr Asp Thr
385                 390                 395                 400

Tyr Lys Leu Ile Leu Asn Gly Lys Thr Leu Lys Gly Glu Thr Thr Thr
                405                 410                 415

Glu Ala Val Asp Ala Ala Thr Ala Glu Lys Val Phe Lys Gln Tyr Ala
            420                 425                 430

Asn Asp Asn Gly Val Asp Gly Glu Trp Thr Tyr Asp Asp Ala Thr Lys
        435                 440                 445

Thr Phe Thr Val Thr Glu Lys Pro Glu Val Ile Asp Ala Ser Glu Leu
    450                 455                 460

Thr Pro Ala Val Thr Thr Tyr Lys Leu Val Ile Asn Gly Lys Thr Leu
465                 470                 475                 480

Lys Gly Glu Thr Thr Thr Glu Ala Val Asp Ala Ala Thr Ala Glu Lys
                485                 490                 495

Val Phe Lys Gln Tyr Ala Asn Asp Asn Gly Val Asp Gly Glu Trp Thr
            500                 505                 510

Tyr Asp Asp Ala Thr Lys Thr Phe Thr Val Thr Glu Lys Pro Glu Val
        515                 520                 525

Ile Asp Ala Ser Glu Leu Thr Pro Ala Val Thr Thr Tyr Lys Leu Val
```

```
    530                 535                 540

Ile Asn Gly Lys Thr Leu Lys Gly Glu Thr Thr Thr Lys Ala Val Asp
545                 550                 555                 560

Ala Glu Thr Ala Glu Lys Ala Phe Lys Gln Tyr Ala Asn Asp Asn Gly
                565                 570                 575

Val Asp Gly Val Trp Thr Tyr Asp Asp Ala Thr Lys Thr Phe Thr Val
            580                 585                 590

Thr Glu


<210> SEQ ID NO 24
<211> LENGTH: 354
<212> TYPE: DNA
<213> ORGANISM: Artificial Sequence
<220> FEATURE:
<223> OTHER INFORMATION: VH for chimeric B1H2

<400> SEQUENCE: 24

gaggtgcagc tgcagcagag cggccctgag ctggtgaagc ccggcgcttc cgtgaagatg     60

agctgcaagg ccagcggcta cacactgaca aattacgtga tgcactggat gaagcagaag    120

cccggccagg gcctggagtg gatcggcttc atcatccctt ttaacgacgg caccaagtac    180

aacgagcact ttaagggcaa ggccacactg acatccgaca agagcagcaa taccgcctac    240

atggtgctgt ccagcctgac cagcgaggac tccgccgtgt actactgtgc caggtacgat    300

tttgagggct acttcgacgt gtggggcgcc ggcaccacag tgaccgtgag cagc          354


<210> SEQ ID NO 25
<211> LENGTH: 321
<212> TYPE: DNA
<213> ORGANISM: Artificial Sequence
<220> FEATURE:
<223> OTHER INFORMATION: VL for chimeric B1H2

<400> SEQUENCE: 25

gacatccaga tgacccagac aacaagcagc ctgagcgcct ccctgggcga cagggtgaca     60

atctcctgca gcgccagcca ggacatcaca aacttcctga actggtatca acagaagccc    120

gacggcacag tgaagctgct gatctactcc acatccagac tgcactccgg cgtgccctcc    180

aggttctccg gctccggatc cggcacagat tactccctga ccatcagcaa cctggagcct    240

gaggacatcg ccacctacta ctgccagcag tacagcaatc tgccttggac ctttggcggc    300

ggcaccaatc tggagatcaa g                                              321


<210> SEQ ID NO 26
<211> LENGTH: 118
<212> TYPE: PRT
<213> ORGANISM: Artificial Sequence
<220> FEATURE:
<223> OTHER INFORMATION: VH for huB1H2-V2, huB1H2-V8, huB1H2-V14, and
      huB1H2-V20

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asn Tyr
            20                  25                  30

Val Met His Trp Val Arg Gln Ala Pro Gly Gln Gly Leu Glu Trp Ile
        35                  40                  45

Gly Phe Ile Ile Pro Phe Asn Asp Gly Thr Lys Tyr Asn Glu His Phe
    50                  55                  60
```

Lys Gly Arg Val Thr Ile Thr Arg Asp Thr Ser Ile Ser Thr Ala Tyr
65 70 75 80

Met Gln Leu Ser Ser Leu Arg Ser Glu Asp Thr Ala Val Tyr Tyr Cys
85 90 95

Ala Arg Tyr Asp Phe Glu Gly Tyr Phe Asp Val Trp Gly Gln Gly Thr
100 105 110

Leu Val Thr Val Ser Ser
115

<210> SEQ ID NO 27
<211> LENGTH: 118
<212> TYPE: PRT
<213> ORGANISM: Artificial Sequence
<220> FEATURE:
<223> OTHER INFORMATION: VH for huB1H2-V3, huB1H2-V9, huB1H2-V15, and huB1H2-V21

<400> SEQUENCE: 27

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Thr Asn Tyr
20 25 30

Val Met His Trp Met Arg Gln Ala Pro Gly Gln Gly Leu Glu Trp Ile
35 40 45

Gly Phe Ile Ile Pro Phe Asn Asp Gly Thr Lys Tyr Asn Glu His Phe
50 55 60

Lys Gly Arg Val Thr Ile Thr Arg Asp Thr Ser Ile Ser Thr Ala Tyr
65 70 75 80

Met Gln Leu Ser Ser Leu Arg Ser Glu Asp Thr Ala Val Tyr Tyr Cys
85 90 95

Ala Arg Tyr Asp Phe Glu Gly Tyr Phe Asp Val Trp Gly Gln Gly Thr
100 105 110

Leu Val Thr Val Ser Ser
115

<210> SEQ ID NO 28
<211> LENGTH: 118
<212> TYPE: PRT
<213> ORGANISM: Artificial Sequence
<220> FEATURE:
<223> OTHER INFORMATION: VH for huB1H2-V4, huB1H2-V10, huB1H2-V16, huB1H2-V22, and huB1H2-V33

<400> SEQUENCE: 28

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Thr Asn Tyr
20 25 30

Val Met His Trp Val Arg Gln Ala Pro Gly Gln Gly Leu Glu Trp Ile
35 40 45

Gly Phe Ile Ile Pro Phe Asn Asp Gly Thr Lys Tyr Asn Glu His Phe
50 55 60

Lys Gly Arg Val Thr Ile Thr Ser Asp Thr Ser Ile Ser Thr Ala Tyr
65 70 75 80

Met Gln Leu Ser Ser Leu Arg Ser Glu Asp Thr Ala Val Tyr Tyr Cys
85 90 95

Ala Arg Tyr Asp Phe Glu Gly Tyr Phe Asp Val Trp Gly Gln Gly Thr
100 105 110

```
Leu Val Thr Val Ser Ser
        115


<210> SEQ ID NO 29
<211> LENGTH: 118
<212> TYPE: PRT
<213> ORGANISM: Artificial Sequence
<220> FEATURE:
<223> OTHER INFORMATION: VH for huB1H2-V5, huB1H2-V11, huB1H2-V17, and
      huB1H2-V23

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asn Tyr
            20                  25                  30

Val Met His Trp Val Arg Gln Ala Pro Gly Gln Gly Leu Glu Trp Ile
        35                  40                  45

Gly Phe Ile Ile Pro Phe Asn Asp Gly Thr Lys Tyr Asn Glu His Phe
    50                  55                  60

Lys Gly Arg Val Thr Ile Thr Arg Asp Lys Ser Ile Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Tyr Asp Phe Glu Gly Tyr Phe Asp Val Trp Gly Gln Gly Thr
            100                 105                 110

Leu Val Thr Val Ser Ser
        115


<210> SEQ ID NO 30
<211> LENGTH: 118
<212> TYPE: PRT
<213> ORGANISM: Artificial Sequence
<220> FEATURE:
<223> OTHER INFORMATION: VH for huB1H2-V6, huB1H2-V12, huB1H2-V18, and
      huB1H2-V24

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asn Tyr
            20                  25                  30

Val Met His Trp Val Arg Gln Ala Pro Gly Gln Gly Leu Glu Trp Ile
        35                  40                  45

Gly Phe Ile Ile Pro Phe Asn Asp Gly Thr Lys Tyr Asn Glu His Phe
    50                  55                  60

Lys Gly Arg Val Thr Ile Thr Ser Asp Lys Ser Ile Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Tyr Asp Phe Glu Gly Tyr Phe Asp Val Trp Gly Gln Gly Thr
            100                 105                 110

Leu Val Thr Val Ser Ser
        115


<210> SEQ ID NO 31
<211> LENGTH: 107
<212> TYPE: PRT
<213> ORGANISM: Artificial Sequence
```

```
<220> FEATURE:
<223> OTHER INFORMATION: VL for huB1H2-V1 - huB1H2-V6

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Thr Asn Phe
            20                  25                  30

Leu Asn Trp Tyr Gln Gln Lys Pro Gly Lys Thr Val Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Ser Asn Leu Pro Trp
                85                  90                  95

Thr Phe Gly Gln Gly Thr Lys Val Glu Ile Lys
            100                 105


<210> SEQ ID NO 32
<211> LENGTH: 107
<212> TYPE: PRT
<213> ORGANISM: Artificial Sequence
<220> FEATURE:
<223> OTHER INFORMATION: VL for huB1H2-V7 - huB1H2-V12

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asn Leu Pro Trp
                85                  90                  95

Thr Phe Gly Gln Gly Thr Lys Val Glu Ile Lys
            100                 105


<210> SEQ ID NO 33
<211> LENGTH: 107
<212> TYPE: PRT
<213> ORGANISM: Artificial Sequence
<220> FEATURE:
<223> OTHER INFORMATION: VL for huB1H2-V13 - huB1H2-V18

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Thr Asn Phe
            20                  25                  30

Leu Asn Trp Tyr Gln Gln Lys Pro Gly Lys Ala Val Lys Leu Leu Ile
        35                  40                  45

Tyr Ser Thr Ser Arg Leu His Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
65 70 75 80

Glu Asp Ile Ala Thr Tyr Tyr Cys Gln Gln Tyr Ser Asn Leu Pro Trp
85 90 95

Thr Phe Gly Gln Gly Thr Lys Val Glu Ile Lys
100 105

<210> SEQ ID NO 34
<211> LENGTH: 107
<212> TYPE: PRT
<213> ORGANISM: Artificial Sequence
<220> FEATURE:
<223> OTHER INFORMATION: VL for huB1H2-V19 - huB1H2-V24

<400> SEQUENCE: 34

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Ser Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Ile Ala Thr Tyr Tyr Cys Gln Gln Tyr Ser Asn Leu Pro Trp
85 90 95

Thr Phe Gly Gln Gly Thr Lys Val Glu Ile Lys
100 105

<210> SEQ ID NO 35
<211> LENGTH: 107
<212> TYPE: PRT
<213> ORGANISM: Artificial Sequence
<220> FEATURE:
<223> OTHER INFORMATION: VL for huB1H2-V33

<400> SEQUENCE: 35

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Ser Thr Ser Arg Leu His Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Ser Asn Leu Pro Trp
85 90 95

Thr Phe Gly Gln Gly Thr Lys Val Glu Ile Lys
100 105